(12) United States Patent
Kawai et al.

(10) Patent No.: US 6,261,245 B1
(45) Date of Patent: Jul. 17, 2001

(54) BODY-FLUID INSPECTION DEVICE

(75) Inventors: Eiji Kawai; Hisao Nishikawa; Kouichi Sonoda; Masao Takinami, all of Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/236,009

(22) Filed: Jan. 22, 1999

(30) Foreign Application Priority Data

Jan. 22, 1998 (JP) .................................. 10-025091
Jun. 30, 1998 (JP) .................................. 10-183794
Oct. 19, 1998 (JP) .................................. 10-296325

(51) Int. Cl.[7] .................................................. A61B 5/00
(52) U.S. Cl. ........................ 600/576; 606/180; 606/181
(58) Field of Search .................................. 600/573, 576, 600/577, 578, 583, 584; 66/181

(56) References Cited

U.S. PATENT DOCUMENTS 4,787,398 * 11/1988 Garcia et al. ...................... 600/583
5,029,583 * 7/1991 Meserol et al. .................... 600/583
6,071,249 * 6/2000 Cunningham et al. ............ 600/578

FOREIGN PATENT DOCUMENTS 0 199 484    10/1986 (EP) .
0 622 046    11/1994 (EP) .

* cited by examiner

*Primary Examiner*—John P. Lacyk
*Assistant Examiner*—Pamela L Wingood
(74) *Attorney, Agent, or Firm*—Burns, Doane, Swecker & Mathis, LLP

(57) ABSTRACT

A body-fluid inspection device, which sticks a skin so as to obtain a fine amount of body fluids and measures ingredients of the body fluids, includes a casing having an opening, a sticking device having a sticking needle that is allowed to protrude from the opening of the casing, and a suction device which places at least portion of a space inside the casing in a reduced-pressure state. Also included are a reduced-pressure releasing device for releasing the space inside the casing from the reduced-pressure state, a chip which is detachably attached to the opening of the casing and is provided with test paper for absorbing the body fluids that have been sucked by the body-fluid suction device, a measuring device for measuring ingredients of the body fluids that have been absorbed by the test paper, and a display device for displaying results of measurements made by the measuring device. The display device is placed on one portion of a surface of the casing. The sticking, the suction and the measuring devices are installed inside the casing.

33 Claims, 23 Drawing Sheets

BODY-FLUID INSPECTION DEVICE

BACKGROUND OF THE INVENTION

The present invention relates to a body-fluid inspection device which draws body fluids (especially, blood) by sticking a needle into the surface of a living body, such as a finger tip, and carries out an inspection, upon inspecting body fluids such as, for example, blood and inter-organ fluids.

Recently, along with an increase in the number of diabetics, it has been proposed that self blood-sugar measurements be carried out by the patients so as to monitor the every-day fluctuation of the blood-sugar value for themselves. At present, in most of the measurements of the blood-sugar value, blood-sugar measuring devices are used in which test paper which changes colors in accordance with the amount of glucose in the blood is prepared, blood is supplied to the test paper so as to be developed therein, and the blood-sugar value is estimated by optically measuring the level of the color that has been developed (measurement of colors). Prior to this type of measurements, the patient has to stick the skin of his or her finger tip by using a sticking tool equipped with a needle or a small knife in order to draw and sample his or her blood; and then the patient has to squeeze blood out by pressing the surrounding area of the stuck portion with the fingers, etc. However, since the sticking tool and the blood-sugar measuring device are separately provided, the patient has to replace the sticking tool in his or her hand with the blood-sugar measuring device while the finger is bleeding; this causes degradation in the operability, and is not preferable from the sanitary point of view.

Here, U.S. Pat. No. 5,279,294 discloses a system in which conventional sticking tool and blood-sugar measuring device are provided as an integral part. In this system, the following means are installed in a housing: a sticking means, a means for transporting blood to a chemical reagent for use in blood and a means for carrying out optical measurements on the chemical reagent for use in blood and for displaying the results thereof. However, in this system, since the amount of blood is not sufficient even if the sticking operation is carried out, the patient has to squeeze blood out by pressing the stuck portion with the fingers, etc. after the sticking operation; this fails to make any improvements in the operability as compared with the conventional devices.

Moreover, another blood-sugar measuring device has been disclosed in Jpn. Pat. Appln. KOKAI Publication No. 276235 in 1997. In this blood-sugar measuring device, a sticking means, a pressure band for pressing the finger and a means for measuring and displaying the blood ingredients are placed in a housing. However, although this blood-sugar measuring device makes it possible to draw a sufficient amount of blood required by the function of the pressure band, remaining blood on the finger tip tends to adhere to the pressure band at the time of withdrawing the finger from the pressure band after use; this causes the possibility of contagion, etc.

BRIEF SUMMARY OF THE INVENTION

Accordingly, an object of the present invention is to provide a body-fluid inspection device which can successively carry out sticking, body-fluid (blood) sampling and measuring processes by using simple operations.

Another object of the present invention is to provide a sticking tool which can be suitably used also in a body-fluid inspection device of the present invention.

According to the present invention, there is provided a body-fluid inspection device, which sticks a skin so as to obtain a fine amount of body fluids and measures ingredients of the body fluids, comprising:

a casing having an opening;

sticking means having a sticking needle that is allowed to protrude from the opening of the casing;

suction means which places at least portion of a space inside the casing in a reduced-pressure state;

reduced-pressure releasing means for releasing the space inside the casing from the reduced-pressure state;

a chip which is detachably attached to the opening of the casing, and provided with test paper for absorbing the body fluids that have been sucked by the body-fluid suction means;

measuring means for measuring ingredients of the body fluids that have been absorbed by the test paper; and display means for displaying results of measurements made by the measuring means, the display means being placed on one portion of a surface of the casing, wherein the sticking means, the suction means and the measuring means are installed inside the casing.

In the present invention, a body-fluid inspection device of the present invention may comprise:

a housing having an opening at the tip end thereof;

sticking means including a sticking plunger that is allowed to shift toward the tip end inside the housing with the sticking needle being attached thereto, and a first pressing means for pressing the sticking plunger toward the tip end;

suction means including a suction plunger that is provided with a seal member having an air-sealed property and that brings the housing to a reduced-pressure state upon shifting toward the base end, and a second pressing means for pressing the suction plunger toward the base end;

air-releasing means for releasing the housing which is in a reduced-pressure state to the atmospheric pressure; and operation means for carrying out at least a sticking process by the sticking needle and a pressure-reducing process on the housing by an operation of the suction plunger, successively in this order or at the same time.

Also in the present invention, a body-fluid inspection device of the present invention may comprise:

a housing having an opening at the tip end thereof;

sticking means including a sticking plunger that is allowed to shift toward the tip end inside the housing with the sticking needle being attached thereto, and a first pressing means for pressing the sticking plunger toward the tip end;

suction means including a suction plunger that is provided with a seal member having an air-sealed property and that brings the housing to a reduced-pressure state upon shifting toward the base end, and a second pressing means for pressing the suction plunger toward the base end;

air-releasing means for releasing the housing which is in a reduced-pressure state to the atmospheric pressure; and operation means which carries out a sticking process by the sticking needle and a pressure-reducing process inside the housing by an operation of the suction plunger, successively in this order or at the same time, and then allows the housing to be released to the atmospheric pressure.

Further, in the present invention, a body-fluid inspection device of the present invention may comprise:

a housing having a tip end that is opened;

a plunger to which a lancet having a sticking needle extending toward the tip end is attached, the plunger being allowed to slide inside the housing;

a stopper connected in the rear end direction of the plunger;

an adjustment mechanism which contacts the stopper; and a sticking-use spring for shifting the lancet, the plunger and the stopper toward the tip end of the housing, the sticking-use spring being connected to the plunger or the stopper, wherein: an engaging section is provided in the inner face of the housing;

a stopping section is formed in at least one of the lancet, the plunger and the stopper, the stopping section being allowed to engage the engaging section so as to stop the lancet, the plunger and the stopper at a first position; and after the lancet, the plunger and the stopper have shifted toward the tip end from the first position by the spring that is released from the engagement between the engaging section and the stopping section, the stopper comes into contact with the adjustment mechanism so that the shift of the lancet, the plunger and the stopper is stopped at a second position.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Referring to Figures, the following description will discuss several preferred embodiments of the body-fluid inspection device of the present invention.

Figure 1:
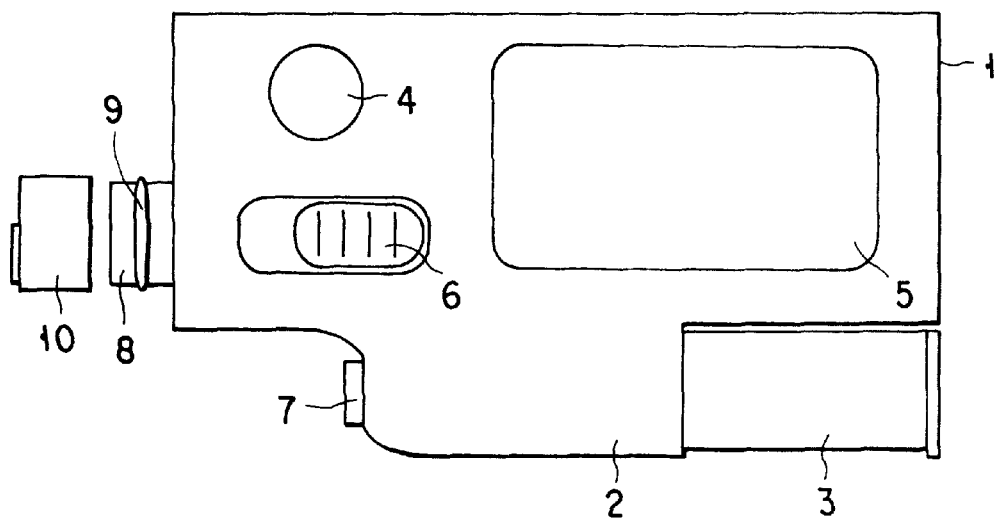
FIG. 1 is a drawing that shows the appearance of a body-fluid inspection device in accordance with one embodiment of the present invention.
Figure 2:
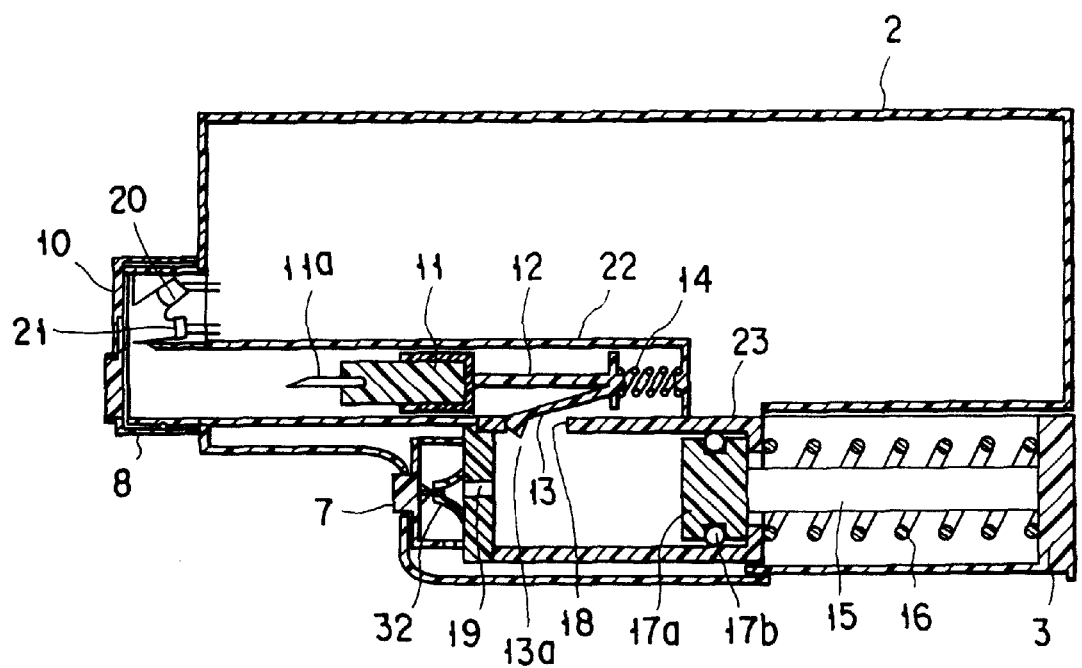
FIG. 2 is a cross-sectional view of the body-fluid inspection device shown in FIG. 1.
Figure 3:
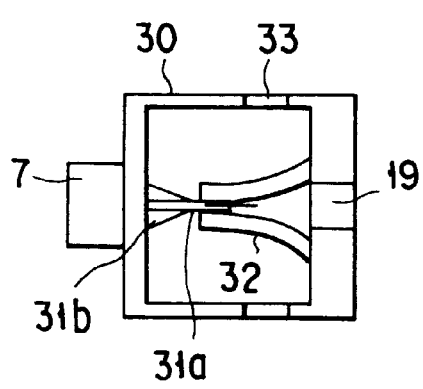
FIG. 3, which shows examples of a pressure-reduction releasing means and an evacuation means in the body-fluid inspection device shown in FIG. 1, is a cross-sectional view showing a state in which reduced pressure is maintained in a casing.
Figure 4:
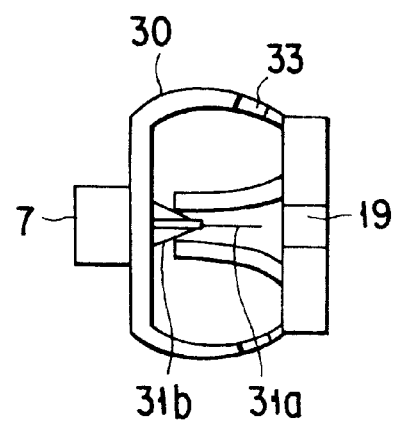
FIG. 4 is a cross-sectional view showing a state in which the pressure-reduction releasing means and the evacuation means of FIG. 3 have been released from the reduced pressure state.
Figure 5:
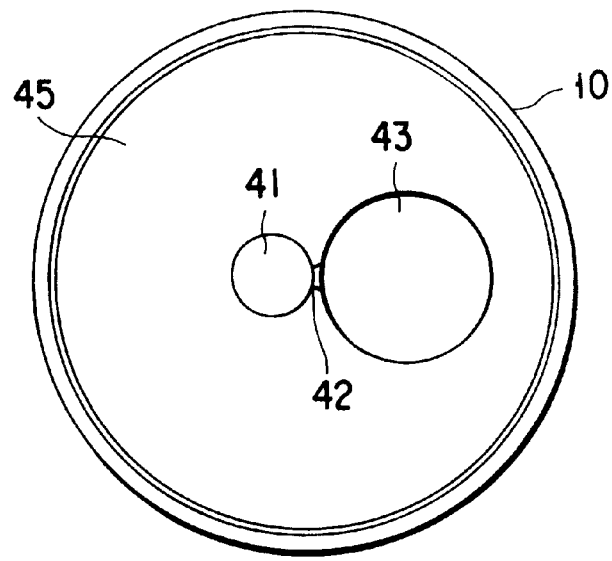
FIG. 5 is a plan view that shows a blood-sampling chip in the body-fluid inspection device in FIG. 1 which is viewed from its opening section.
Figure 6:
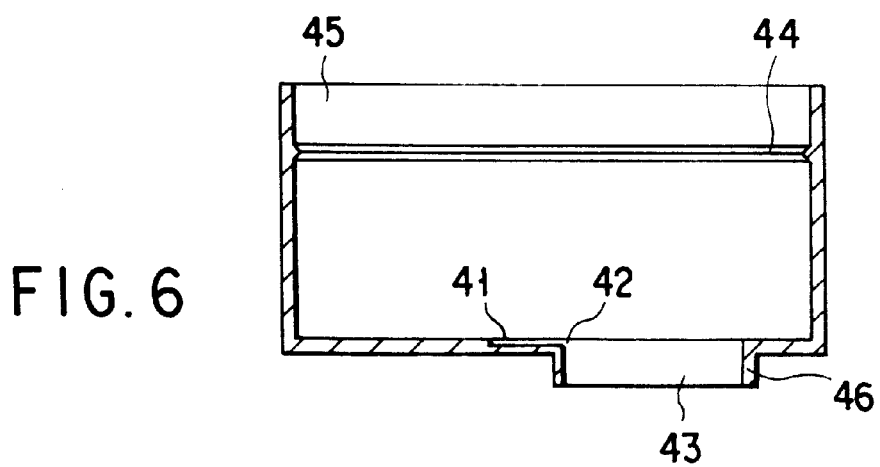
FIG. 6 is a cross-sectional view of the blood-sampling chip shown in FIG. 5.

FIG. 1 is a front view that shows one example of the body-fluid inspection device of the present invention, FIG. 2 is a cross-sectional view of the body-fluid inspection device shown in FIG. 1, FIG. 3 is a cross-sectional view that shows a state in which reduced pressure is maintained in a casing in the structural examples of the reduced-pressure releasing means and evacuation means, FIG. 4 is a cross-sectional view that shows a state in which the reduced-pressure releasing means and the evacuation means in the structural examples are being released from the reduced-pressure state, FIG. 5 is a plan view that shows a blood-sampling chip when viewed from the opening section coupled to a blood-sampling chip connecting section, and FIG. 6 is a cross-sectional view of the blood-sampling chip shown in FIG. 5. The following explanation will be given, supposing that a body-fluid inspection device 1 measures the blood-sugar value as one ingredient of body fluids.

As illustrated in FIG. 1, the body-fluid inspection device 1 is shown as being provided with a casing 2, a plunger cover 3, a reduced-pressure releasing button 7 for releasing a reduced pressure state, a blood-sampling chip 10 (coupled to a blood-sampling chip connecting section 8 in FIG. 2), a blood-sampling chip connecting section 8 for securing the blood-sampling chip 10, a blood-sampling chip releasing lever 6 for removing the blood-sampling chip 10, a power switch 4, a display 5 for displaying the results of measurements, and an elastic member 9 for allowing the blood-sampling chip 10 to be engaged and stopped by the connecting section 8 in a vacuumed state.

As illustrated in FIG. 2, inside the casing 2 are disposed a suction sticking mechanism consisting of a lancet 11 having a sticking needle 11a, a lancet holder 12, a first spring 14, a plunger 15, a second spring 16, a gasket 17a, and other members, a measuring mechanism (of which only a photo-emmisive means 20 and a photoelectric means 21 are shown), and a display mechanism (not shown).

The suction/sticking mechanism is constituted by a sticking mechanism and a suction mechanism. As illustrated in FIG. 2, the sticking mechanism is constituted by the lancet 11 having the sticking needle 11a, the lancet holder 12 for holding the lancet 11, an engaging member 13 that is integral with the lancet holder 12 and has an engaging section 13a at its end, and the first spring 14 for pressing the lancet holder 12 from its rear end face, and these members 11, 12, 13 and 14 are accommodated in a sticking-device housing 22. One end of the first spring 14 is secured to the rear end of the lancet holder 12, while the other end is secured to a wall surface inside the sticking-device housing 22. Here, instead of the first spring 14, an elastic member that can push the lancet holder 12 out, such as a rubber member, may be adopted.

As illustrated in FIG. 2, the suction mechanism is, on the other hand, constituted by the plunger 15 and the gasket 17a that is used for allowing the inside wall of the suction housing 23 to slide along the tip end of the plunger 15 in an air-sealed manner, and these members 15 and 17a are accommodated in the suction housing 23.

In the body-fluid inspection device 1 as shown in the Figures, the sticking-device housing 22 and the suction housing 23 are installed side by side, and are designed so that the respective inner spaces communicate with each other through a side hole 18. The tip end of the sticking-device housing 22 is in an open state, and the blood-sampling chip connecting section 8 is placed along the tip end. The rear end thereof is in a closed state, and the first spring 14 connecting to the lancet holder 12 is secured to its inner surface. Here, in the present body-fluid inspection device 1, the first spring 14 is fixed between the rear-end face of the sticking-device housing 22 and the lancet holder 12, as shown in FIG. 2. so as to form a structure for pushing the lancet holder 12 out; however, it may be fixed between the tip end of the sticking housing 22 and the lancet holder 12 so as to form a structure for drawing the lancet holder 12 out.

The suction housing 23 has a communicating hole 19 in its tip end, and the gasket 17a, which slides along the inner wall in an air-sealed state, is sealed inside thereof. A non-return valve 32 is installed on the outside section of the suction housing 23 so as to form an evacuation means which, upon a high pressure state inside the sticking-device housing 22 and the suction housing 23, releases air corresponding to the excessive pressure. Here, the communicating hole 19 and the non-return valve 32 may be installed on the side face of the suction housing 23. The plunger 15, which extends toward the rear end of the suction housing 23, is attached to the gasket 17a. Moreover, an O ring 17b is preferably installed along the circumferential surface of the gasket 17a so as to enhance its sliding property and air-sealing property.

In the body-fluid inspection device 1 as shown in the Figures, the sticking-device housing 22 and the suction housing 23 are installed in parallel with each other; however, they may be installed in series with each other. In this case, a hole, which corresponds to the side hole 18, is formed from the rear end of the sticking-device housing 22 to the tip end of the suction housing 23, and the engaging section 13 is engaged and stopped by this hole, and is released from its engagement by contacting the gasket 17a, with the communicating hole being formed in the side face of the housing. Additionally, when the sticking-device housing and the suction housing are installed in series with each other, the body-fluid inspection device tends to become longer in its entire length; however, it is possible to shorten the entire length by making both or either of the sticking-device housing 22 and the suction housing 23 thicker and shorter, and adjusting the respective components to be housed in the respective housings to corresponding sizes.

Although not shown in the Figures, a rod-shaped member is installed in parallel with the sticking-device housing 22 between the outer surface of the sticking-device housing 22 and the inner surface of the casing 2 in such a manner that its one end is secured to the inside of a blood-sampling chip release lever 6 on the surface of the casing 2, while the other end is allowed to stick out by shifting the blood-sampling chip release lever 6, and is further allowed to contact the blood-sampling chip 10 in such a sticking-out state, so as to separate it from the blood-sampling chip connecting section 8.

Additionally, the cross-sectional shapes of the sticking-device housing 22 and the suction housing 23 are not specifically limited, and may be formed into round, square, or other polygon shapes. The gasket 17a is preferably formed into the same shape as the inner-surface shape of the suction housing.

The blood-sampling chip connecting section 8 is installed in the body-fluid inspection device 1. In FIG. 2, the blood-sampling chip connecting section 8 sticks out from the casing 2 as a cylinder so as to surround the opening of the tip end of the sticking-device housing 22 in the form of double circles, and the blood-sampling chip 10 is fitted thereto in a covering manner. Moreover, inside the cylindrical blood-sampling chip connecting section 8 are installed a photoemmissive device 20 and a photoelectric device 21 that serve as a measuring mechanism in addition to the tip end of the sticking-device housing 22.

Moreover, as shown in FIG. 1, a ring-shaped elastic member 9 is installed along the outer surface of the blood-sampling chip connecting section 8 in contact therewith so as to positively engage and stop the blood-sampling chip 10 in an air-sealed state.

The blood-sampling chip connecting section 8 is not intended to be limited to the above-mentioned embodiment. For example, it may have a structure that continuously extend from the tip end without surrounding the tip end of the sticking-device housing 22, or is not necessarily provided as a structure that protrudes from the casing 2. In other words, any structure is adopted as long as it can be fitted to the blood-sampling chip 10 in an air-sealed state, and as long as, when reduced pressure is applied to the sticking-device housing 22 and the suction housing 23 with the skin of a subject being put on a suction opening 43 (see FIG. 5) of the blood-sampling chip 10, the reduced pressure state is maintained. In this case, the shape of the blood-sampling chip 10 is not intended to be limited to the shape as shown in FIG. 4 or FIG. 5.

In the body-fluid inspection device 1, the photoemmissive device 20 and the photoelectric device 21 are installed as a measuring mechanism so that the sugar ingredient in the blood is allowed to develop colors by a color reaction through a method that will be described later, and so that the blood-sugar value is calculated by measuring the degree of light absorption and displayed. Here, although no specific means for calculating the blood-sugar value and for displaying the value are shown in the Figures, a conventional blood-sugar calculating means for calculating the blood-sugar value by using a similar means and a conventional display means can be adopted. Moreover, in the present invention, the measuring means is not intended to be limited to a means for allowing the sugar ingredient in the blood to develop colors by a color reaction as will be described later and for measuring the degree of light absorption; and other means for making a direct contact of the sample or for measuring the blood-sugar value by allowing light with a predetermined wavelength to pass through the sample may be adopted. In these cases, a sensor, etc., which is suitable for the means may be used in lieu of the photoemmissive device 20 and the photoelectric device 21.

Referring to FIGS. 5 and 6, the following description will discuss the blood-sampling chip 10 used in the body-fluid inspection device 1 in detail. FIG. 5 is a plan view that shows the blood-sampling chip 10 that is viewed from an opening 45 that fits to the blood-sampling chip connecting section 8 of the blood-sampling chip 10, and FIG. 6 is a cross-sectional view of the blood-sampling chip 10 shown in FIG. 5.

The blood-sampling chip 10, which has a cylindrical shape, is provided with a bottom face on its one end in which the suction opening 43 for sucking the skin upon contact with the skin and upon reduced pressure of the sticking-device housing 22 and the suction housing 23 is installed, and an opening 45 on the other end that fits to the blood-sampling chip connecting section 8. Test paper 41 used for absorbing body fluids serving as a sample is placed by the side of the suction opening 43 (in the vicinity of the center of the bottom surface), and a groove 42 serving as a body-fluid (blood) guiding means for guiding body fluids from the suction opening 43 to the test paper 41 through the surface tension is also formed. In this manner, even based upon a small amount of sampled body fluids, it becomes possible to carry out an effective inspection. The shape, size and length of the groove 42 are not specifically limited; and they are appropriately selected in accordance with the size and shape of the test paper 41 and the suction opening 43. Here, in the present invention, the blood-sampling chip 10 is not intended to be limited to the cylinder shape, and may be provided as a square shape in its cross-section, a cylinder having a polygonal shape in its cross-section or a conical shape whose diameter narrows toward its one end.

The diameter of the suction opening 43 is not particularly limited, and may be set at any size as long as it is larger than a minimum size that allows the sucked skin to form an appropriate mound shape from which blood is absorbed. Further, the shape is not particularly limited, and may be provided as a square or another polygonal shape. Specifically, the suction opening is preferably set so as to have an opening diameter of 4 to 10 mm so as to come into contact with the surface of a living body, such as the finger tip, upper arm, abdomen, thigh, and an ear-lobe and to allow a desired blood absorbing process independent of individual differences such as sex, age, etc. and differences in portions to be stuck; and in particular, if the portion to be stuck is an ear-lobe, it is preferably set in the range of 4 to 6 mm. It is also preferably formed into a shape, such as a pipe shape, which can stimulate the periphery of the portion to be stuck when pressed onto the surface (skin) of a living body. This is because the stimulation on the periphery of the portion to be stuck makes it possible to alleviate pain at the time of sticking.

More specifically, as illustrated in FIG. 6, a cylinder member 46 is preferably attached to the circumferential edge of the suction opening 43. Moreover, this cylinder member 46 makes it possible to prevent air from flowing into the sticking-device housing 22 and the suction housing 23 through the gap between the blood-sampling chip 10 and the skin when the sticking-device housing 22 and the suction housing 23 are maintained in a reduced pressure state. In order to maintain visibility of the inside of the blood-sampling chip 10, that is, in order to allow visual confirmation of the bleeding state after the sticking operation, the blood-sampling chip 10 is preferably constituted by a transparent or translucent material.

The shape and size of the opening 45 are not particularly limited, and any shape and size thereof are used as long as the opening 45 is fitted to the blood-sampling chip connecting section 8 in an air-sealed state. Additionally, it is preferable to form a ring-shaped protrusion 44 along the inner circumferential face of the opening 45; this makes it possible to connect the blood-sampling chip 10 and the blood-sampling chip connecting section 8 more firmly in an air-sealed state by an interactive function with the elastic member 9 installed in the blood-sampling chip connecting section 8.

The shape and size (including the thickness) of the test paper 41 are not particularly limited; however, when it is too large, there may be a possibility that measurements become inoperative in the case of a small amount of absorbed sample, or when it is too small, the sample might not be absorbed appropriately. Taking these into consideration, the test paper 41 is appropriately selected. The position of the test paper 41 is not particularly limited, as long as it is close to the suction opening 43 and allows the measuring mechanism to sense the test paper. In FIGS. 5 and 6, the test paper 41 is located in the vicinity of the center of the bottom face with the suction opening 43 being located on its side; however, the layout may be reversed, or the centers of the test paper 41 and the suction opening 43 may be located in the vicinity of the center of the bottom face.

The material and mode of the test paper 41 are not particularly limited, and nonwoven fabric, etc. which have been conventionally used as body-fluid testing materials may be utilized. Moreover, since the body-fluid inspection device 1 is designed to measure the blood-sugar value (glucose concentration) by the use of a color reaction, a reagent for allowing an enzyme such as glucose oxidase and/or its decomposed products to develop colors is fixed to the test paper 41. In the present invention, the measuring method is not intended to be limited to the measurements of the degree of light absorption by the use of the color reaction, and when another measuring method is used, the measuring mechanism may be provided with another appropriate device, such as a sensor, instead of the above-mentioned photoemmissive device 20 and the photoelectric device 21.

In the body-fluid inspection device 1, the communicating hole 19 is formed in the suction housing 23 as one element of the reduced-pressure releasing means for releasing the reduced-pressure state after a reduced pressure has been applied to the sticking-device housing 22 and the suction housing 23 in order to suck the skin and also to suck body fluids. Moreover, the communicating hole 19 also serves as one element of the evacuation means which, in the case of a pressurized state of the sticking-device housing 22 and the suction housing 23 at the time of the sticking process, releases air corresponding to the excessive pressure.

The following description will discuss the reduced-pressure releasing means and the evacuation means of the body-fluid inspection device 1 more specifically.

As illustrated in FIGS. 3 and 4, the reduced-pressure releasing means and the evacuation means are integrally formed in the body-fluid inspection device 1. FIG. 3 shows a cross-sectional view of the suction housing 23 when it is in a normal state or in a reduced-pressure state, and FIG. 4 is a cross-sectional view showing a state in which the suction housing 23 is releasing the reduced-pressure state.

The reduced-pressure releasing means and the evacuation means are respectively installed in a flexible housing 30. The housing 30 is provided with a reduced-pressure releasing button 7 and a vent hole 33.

The reduced-pressure releasing means is constituted by the communicating hole 19, a driver 31a having a shape like the tip end of a minus screwdriver and a wedge member 31b attached to the base end thereof. The evacuation means is constituted by the communicating hole 19 and the non-return valve 32. The driver 31a has a needle shape, and the wedge member 31b consists of several sheets of triangular plates. The non-return valve 32 has an opening at the top of its flexible conical body. Here, in the present invention, the driver 31a, the wedge member 31b and the non-return valve 32 are not intended to be limited to these shapes, and the reduced-pressure releasing means and the evacuation means may be provided as independent parts.

In the normal state or the reduced-pressure state (FIG. 3) of the suction housing 23, the reduced-pressure releasing means is maintained in a reduced-pressure state since the reversal stopping valve and its opening are sealed with the driver 31a. Thereafter, when the suction process of the skin becomes unnecessary, the reduced-pressure releasing button 7 is depressed. This allows the driver 31a and the wedge member 31b to open the non-return valve 32 in a reverse direction, with the result that air flows into the sticking-device housing 22 and the suction housing 23 from the vent hole 33 via the communicating hole 19, thereby releasing the reduced-pressure state.

The evacuation means is arranged so that when the sticking-device housing 22 and the suction housing 23 are brought into a pressurized state by sliding the gasket 17a inside the suction housing 23 at the time of sticking, the non-return valve 32 is allowed to open by the pressure so that air corresponding to the excessive pressure is released from the communicating hole 19 via the vent hole 33.

Figure 7:
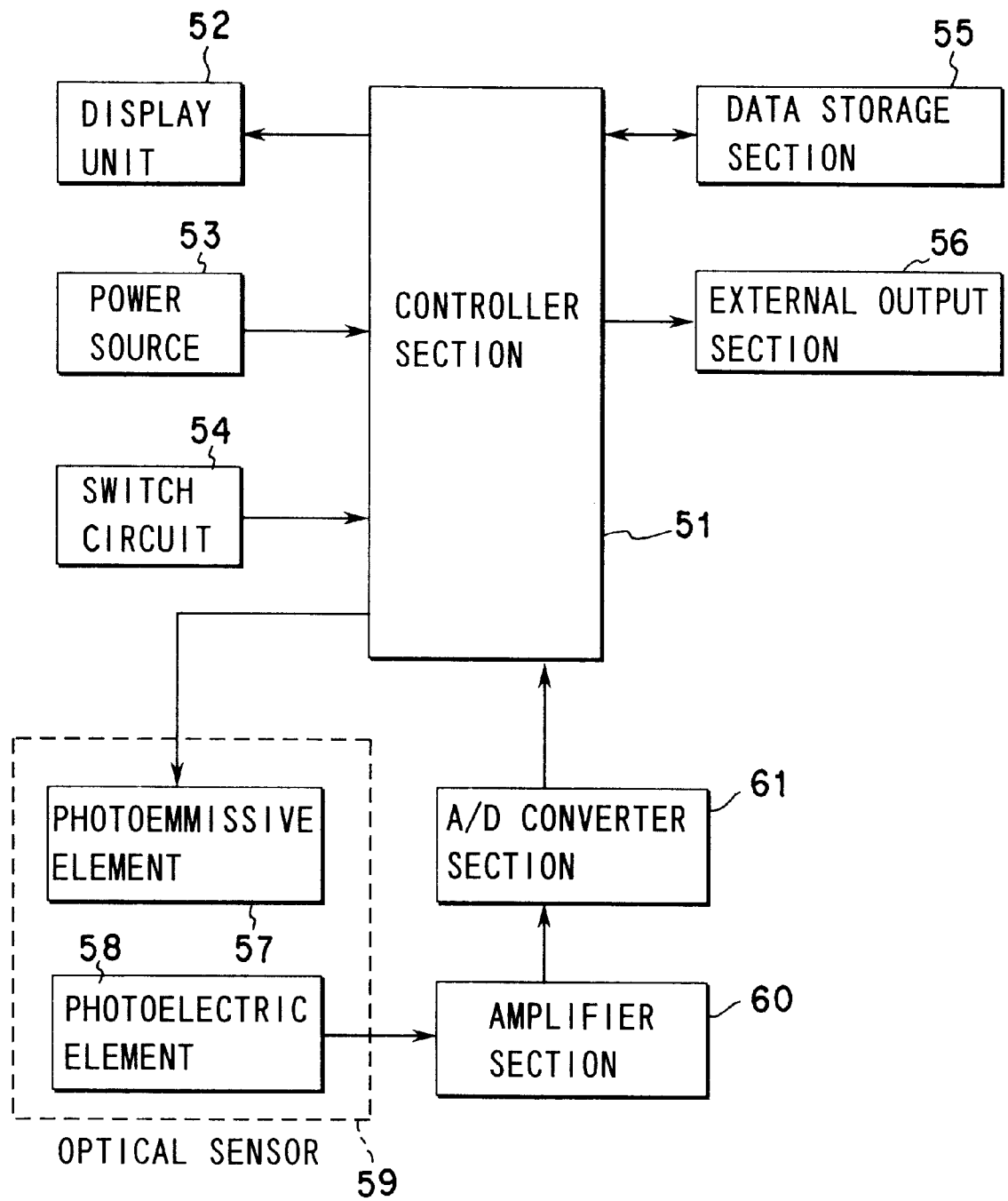
FIG. 7 is a block diagram that shows one example of an inner electric circuit in the body-fluid inspection device of the present invention.

FIG. 7 shows one example of the body-fluid ingredient measuring circuit of the body-fluid inspection device of the present invention. The measuring circuit is provided with a control device 51 such as a CPU, and to the control device 51 are connected a display device 52 (corresponding to the display 5 in FIG. 1), a power-source section 53 (which is connected to the power switch in FIG. 1), a switching circuit 54, a data storage section 55 and an external output section 56. Moreover, an optical sensor 59 constituted by a photoemmissive element 57 (corresponding to the photoemmissive means 20 in FIG. 2) and a photoelectric element 58 (corresponding to the photoelectric means 21 in FIG. 2) is connected to the control device 51. The photoemmissive element 57, when driven by a signal from the control device, projects light having a given wavelength onto test paper (not shown) which has absorbed blood, and reflected light is received by the photoelectric element 58. The received light is amplified by an amplifier 60, and inputted to the control device through an A/D converter 61; thus, the control device 51 calculates the blood-sugar value from the input signal based upon data stored in the data storage section 55, and allows the display device 52 to display the results.

The following description will discuss a method for using the body-fluid inspection device 1.

After the lancet 11 has been attached to the lancet holder 12, the lancet holder 12 is pushed into the sticking-device housing 22 until the engaging section 13 is engaged by the side hole 18. At this time, the first spring 24 is maintained in a compressed state. Next, the blood-sampling chip 10 is attached to the blood-sampling chip connecting section 8 in the main body casing 2. Then, the power switch 4 of the body-fluid inspection device 1 is turned on. Here, the power switch may be turned on before the blood-sampling chip 10 has been attached. Moreover, a switch may be designed so as to automatically turn on the power upon attaching the blood-sampling chip 10, and in this case, the power switch 4 is not required.

Next, the suction opening 43 at the tip of the blood-sampling chip is pressed onto the skin of the subject at a portion to be stuck, and upon pressing the plunger cover 3, the gasket 17a is shifted inside the suction housing 23 in an air-sealed state through the plunger 15 that moves in cooperation with the plunger cover 3. When it is pushed to reach the farthest position, the gasket 17a or the O ring 17b pushes the engaging section 13, thereby removing the engagement; thus, the first spring 14, which has been in a compressed state, is released so that the lancet 11 and the lancet holder 12 is allowed to advance toward the suction opening of the blood-sampling chip 10 and carry out a sticking operation. In this case, when the sticking-device housing 22 and the suction housing 23 are brought into a pressurized state by the slide of the gasket 17a inside the suction housing 23 in an air-sealed state, the non-return valve 32 is opened by the pressure so that air corresponding to the excessive pressure is released from the communicating hole 19 via the vent hole 33. After the sticking operation, the lancet holder 12 to which the lancet 11 is attached is allowed to return to its original position corresponding to the natural length of the spring by the damping function of the spring. In this case, it is preferable to select a spring having an appropriate spring constant so as to prevent double sticking.

Lastly, when the pressing force is removed from the plunger cover 3 with the suction opening 43 of the tip of the blood-sampling chip being pressed onto the skin, the gasket 17a is allowed to retreat by the function of the second spring 16 through the plunger 3 that moves in cooperation with the plunger cover 3, thereby bringing the sticking-device housing 22 and suction housing 23 into a reduced-pressure state so that body fluids are sucked from the stuck portion. Here, the minimum pressure inside the space in the reduced-pressure state is preferably set at approximately −300 mmHg with respect to the atmospheric pressure. This makes it possible to suck a required amount of body fluids in a short time. Then, the body fluids sucked onto the skin are transmitted through the guiding groove 42 formed in the inner wall of the blood-sampling chip 10 by the capillary phenomenon, and absorbed into the test paper 41.

Thereafter, light having a given wavelength is projected from the photoemmissive means 20 onto the blood absorbed in the test paper 41, the reflected light is sensed by the photoelectric means 21, the blood-sugar value is measured, and the results are displayed on the display 5. Additionally, after the blood has been absorbed in the test paper 41, the reduced-pressure releasing button 7 is pressed so that external air is introduced into the sticking-device housing 22 and the suction housing 23, and the body-fluid inspection device 1 is removed when the sense of being sucked disappears from the skin.

As described above, the present invention provides a body-fluid inspection device in which a sticking tool and a measuring device for a body-fluid ingredient (for example, blood-sugar value) are formed into an integral device. As compared with the application of conventional sticking tool and body-fluid measuring device, the body-fluid inspection device of the present invention provides an efficient operation and is superior in sanitation. Moreover, the body-fluid inspection device of the present invention carries out a suction operation on the periphery of a portion to be stuck on the skin of the subject, with the inside of the device being maintained in a reduced-pressure state so as to accelerate the flow of body fluids; therefore, even with superficial sticking with less pain, an amount of body fluids required for an inspection, etc., can be readily obtained, and measured.

Figure 12:
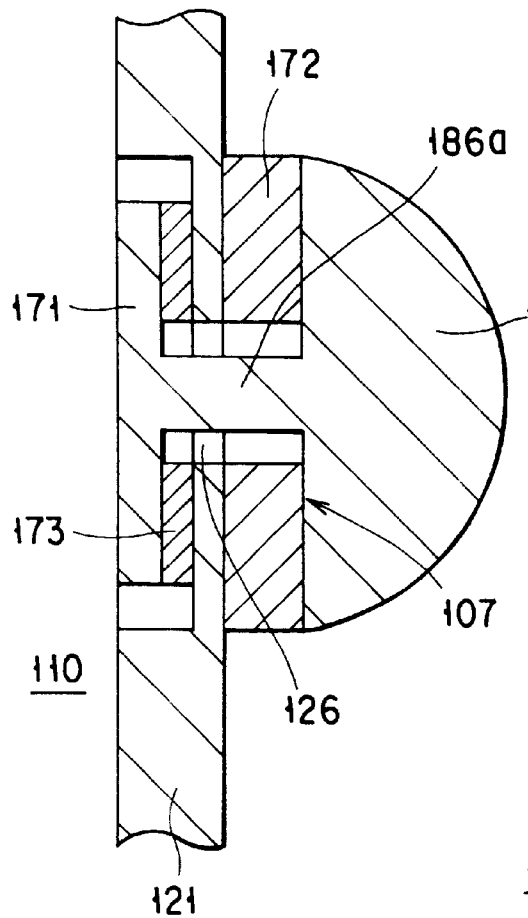
FIGS. 12 and 13 are cross-sectional views of a construction of an air-releasing means which can be used in the sticking tool of FIG. 8 in different states.
Figure 13:
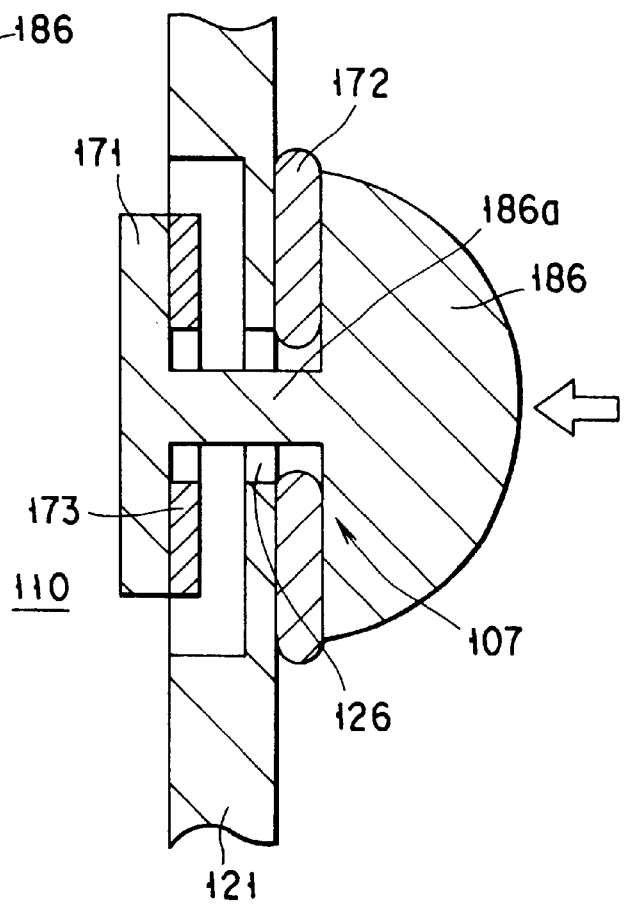

Next, referring to FIGS. 8 through 13, an explanation will be given of one example of a sticking tool that is preferably used in the body-fluid inspection device of the present invention. FIGS. 8, 9, 10 and 11 are cross-sectional side views that show the sticking tool of the present invention in respectively different states; and FIG. 12 and FIG. 13 are cross-sectional views that show a structural example of the air-releasing means. Here, upon explanation, in FIGS. 8 through 11, the upper side is referred to as "base end" and the lower side is referred to as "tip end".

As illustrated in FIGS. 8 through 13, the present sticking tool (blood-sampling sticking tool) 101A is provided with a housing 102, a sticking plunger 103, a coil spring (first pressing means) 104 for pressing the sticking plunger 103 in the tip-end direction, a suction plunger 105, a coil spring (second pressing means) 106 for pressing the suction plunger 105 in the base-end direction, an air-releasing valve (air-releasing means) 107 and an operation means 108.

The housing 102 is constituted by a cylinder-shaped housing main body 121 and a cap 122 that is attached to the tip end of the housing main body 121 so as to be freely detached. The housing main body 121 and the cap 122 are made of a material that virtually does not transmit air.

Moreover, a seal ring 123, made of an elastic material, is inserted and sandwiched between the housing main body 121 and the cap 122 so that the cap 122 is attached to the housing main body 121 in an air-sealed state.

The housing main body 121 is designed to house the sticking plunger 103 which will be described later in detail, the coil spring 104, the suction plunger 105 and the coil spring 106, and also serves as a holding portion when the sticking tool 101A is used.

The cap 122, which is a tube-shaped member, has a taper section 122b that narrows its inner and outer diameters toward the tip end.

The tip end of the cap 122 is a portion that is to come into contact with the surface of a living body, such as, for example, the finger tip, upper arm, abdomen, thigh or ear-lobe, and is provided with a tip opening 122a. This tip opening 122a has its opening diameter (opening area) properly adjusted so that a desired suction blood sampling can be carried out independent of individual differences such as sex, age, etc. and differences in portions to be stuck. Specifically, the opening diameter of the tip opening 122a is preferably set in the range of 4 to 10 mm, and is more preferably set in the range of 4 to 6 mm in the case when the finger or ear-lobe is used as the portion to be stuck.

The outer edge of the tip end of the cap 122 is formed into a shape that is suitable for stimulating the periphery of the portion to be stuck and for alleviating pain at the time of sticking when it is pressed onto the surface of a living body (the skin). The shape is also suitable for preventing air from flowing into the housing 102 between the cap 122 and the surface of a living body when the housing 102 is in a reduced-pressure state.

In order to maintain visibility of the inside, more specifically, in order to allow visual confirmation of the bleeding state after the sticking operation, the cap 122 is preferably made of a transparent or translucent material.

An opening 124 through which the suction plunger 105 is inserted is formed at the base end of the housing main body 121. Moreover, side holes 125 and 126, which respectively correspond to a sticking- and suction-use operation button 184 and an air-releasing-use operation button 186 that will be described later, are formed in the side wall of the housing main body 121.

Furthermore, a partition plate 127 is placed inside the housing main body 121. The partition plate 127 is fixedly secured to the side wall of the housing main body 121, or is integrally formed therewith.

A guide groove 128 is formed in the side-wall inner surface of the housing main body 121 in the length direction of the housing main body 121. A stopper 129 with which a protruding portion 134 comes into contact is formed at the tip end of the guide groove 128 (see FIG. 9).

A sticking mechanism, constituted by the sticking plunger 103 and the coil spring 104 for pressing the sticking plunger 103 toward the tip end, is placed inside the housing main body 121.

The sticking plunger 103 is constituted by a needle holder (lancet holder) 131 to which the lancet 111 having the sticking needle 112 is detachably attached, an elastic member 132 that is integrally formed with the needle holder 131 with a first engaging section 133 provided at its end (on the base-end side), and a protruding portion 134 that is integrally formed with the needle holder 131.

Figure 8:
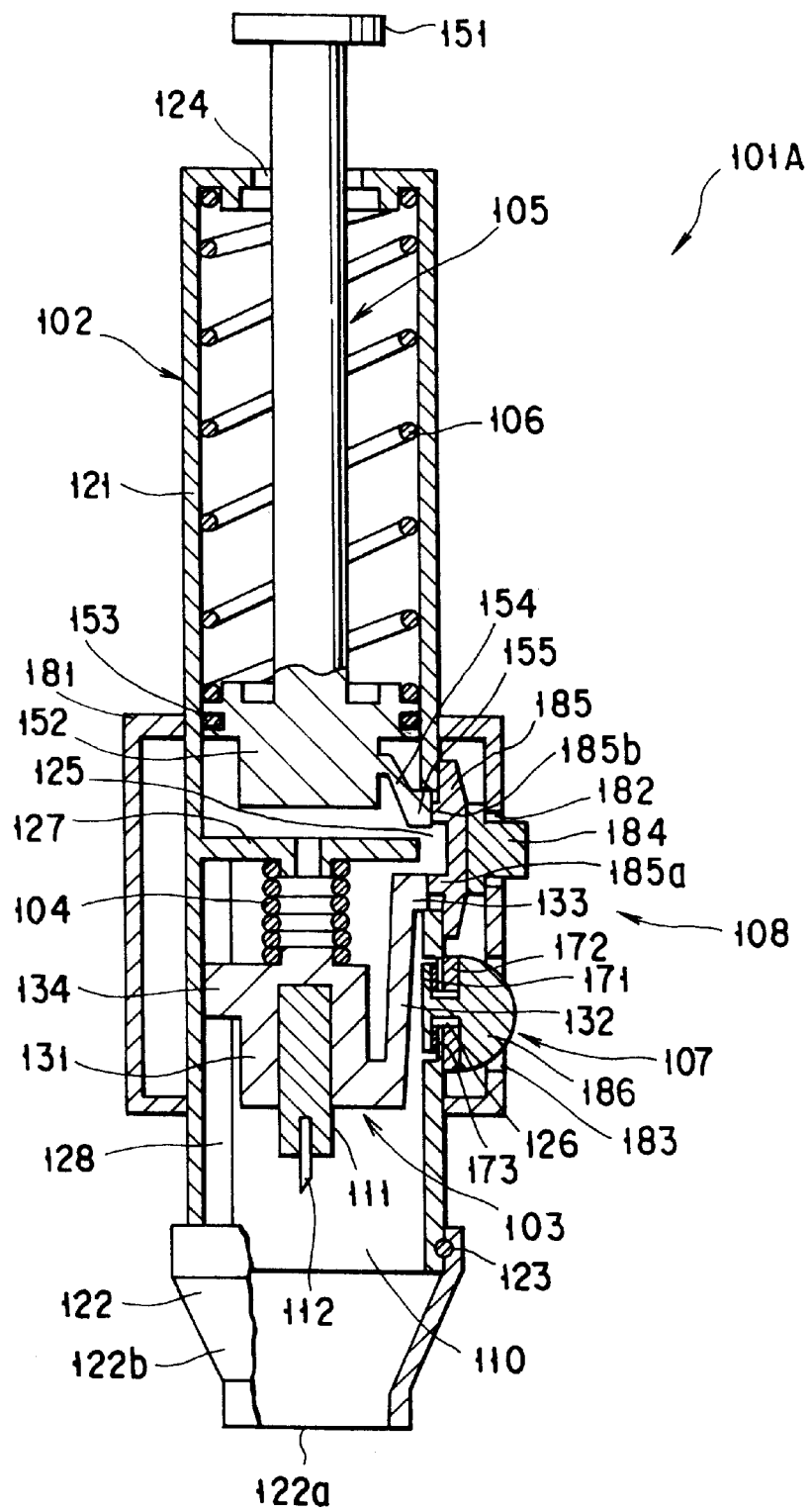
FIG. 8 shows one example of a sticking tool that is preferably used in the body-fluid inspection device of the present invention, and is a cross-sectional view that shows a state prior to the sticking process to the surface of a living body.

The first engaging section 133 is pressed to the right in FIG. 8 by the elastic force of the elastic member 132, and is engaged by the edge of the side hole 125; thus, the sticking plunger 103 is restricted in its shift toward the tip end.

When the sticking tool 101A is not used (in a state prior to sticking), the coil spring 104 is in a compressed state, and its respective ends are secured to the partition plate 127 and the base-end face of the needle holder 131 so that the sticking plunger 103 is pressed toward the tip end.

The protruding portion 134 is inserted into the guide groove 128, and allowed to slide in the length directions of the guide groove 128. Thus, the sticking plunger 103 is shifted inside the housing 102. In this case, the protruding portion 134 comes into contact with the stopper 129, thereby restricting the sticking plunger 103 in its shift toward the tip end. In other words, the setting position of the stopper 129 makes it possible to adjust the sticking depth on the surface of a living body by the sticking needle 112 (=maximum protruding length of the sticking needle 112 from the tip opening 221) (see FIG. 9).

Additionally, the coil spring 104 is properly set so as to have an appropriate elastic coefficient (spring constant) so as not to again stick the surface of a living body during its damping movements after the sticking needle 112 has stuck the surface of the living body.

Moreover, a suction mechanism (negative-pressure generation mechanism), which is constituted by the suction plunger 105 and the coil spring 106 for pressing the suction plunger 105 toward the base end, is installed in the housing main body 121.

The suction plunger 105 is a rod-shaped member, and provided with a handling section 151 on its base end and a gasket 152 on its tip end. The gasket 152 has a seal ring (sealing member) 153 made of an elastic material along its peripheral portion.

The seal ring 153 contacts the inner circumferential face of the housing main body 121 in an air-sealed state, and when the suction plunger 105 is shifted in a length direction of the housing main body 121, the seal ring 153 also shifts in the same direction along the inner circumferential face of the housing main body 121 in an air-sealed state. In this case, the seal ring 153 is preferably set to exhibit a sliding resistance to a degree not to disturb the expansion and shrinkage of the coil spring 106.

An elastic member 154, which is elastically deformable, is formed on the side face of the gasket 152 in a protruding manner, and a second engaging section 155 is formed on its tip end. The second engaging section 155 is pressed to the right in FIG. 8 by the elastic force of the elastic member 154, and is engaged by the edge of the side hole 125; thus, the suction plunger 105 is restricted in its shift toward the base end.

The respective ends of the coil spring 106 are fixed to the base end of the housing main body 121 and the gasket 152. When the sticking tool 101A is not used (in a state prior to sticking), the coil spring 106 is in an extended state so that the suction plunger 105 is pressed toward the base end by its elastic force.

In the suction plunger 105, the seal ring 153 of the gasket 152 contacts the inner circumferential face of the housing main body 121 in an air-sealed state, and the side holes 125 and 126 are also sealed in an air-sealed state; therefore, when the suction plunger 105 is shifted toward the base end with the tip opening 122a being sealed on the surface of a living body, a space 110 inside the housing 102, surrounded by the housing 102 and the gasket 152, is brought to a reduced-pressure state (negative-pressure state).

The air-releasing means is used for releasing the space 110 inside the housing 102 kept in the reduced-pressure state to the atmospheric pressure, and in the present embodiment, it is provided as an air-releasing valve 107 that is manually opened and closed.

As illustrated in FIG. 12 and FIG. 13, the air-releasing valve 107 is constituted by a disc-shaped valve member 171 that is connected to or integrally formed with the shaft 186a of the operation button 186, an elastic member 172 which has a C-letter shape (a shape of a ring with a cut-out in its one portion) and presses the operation button 186 and the valve member 171 to the right in FIG. 1, and a ring-shaped seal pad (seal member) 173 which is secured to the valve member 171 and made of an elastic material.

As illustrated in FIGS. 8 and 12, in a state where the operation button 186 is left untouched, the operation button 186 and the valve member 171 are pressed to the right in FIG. 8 and FIG. 12 by the elastic force of the elastic member 172; thus, the seal pad 173 is pressed and comes into contact with the inner face of the housing main body 121 located on the periphery of the side hole (vent opening) 126 so that the side hole 126 is sealed in an air-sealed state.

Figure 11:
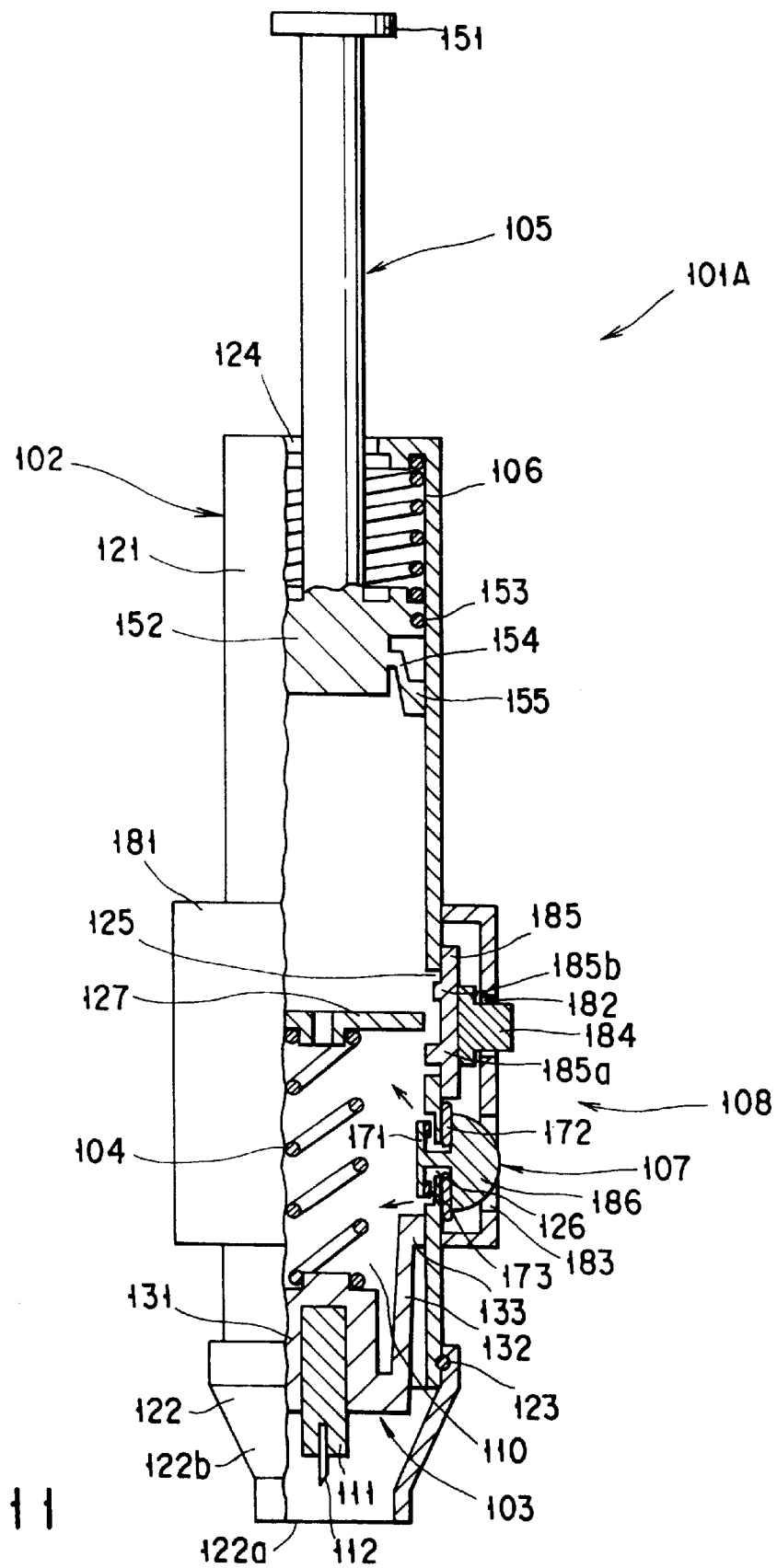
FIG. 11 is a cross-sectional view of the sticking tool of FIG. 8 in still another state.

As illustrated in FIG. 11 and FIG. 13, when the operation button 186 is pressed to the left in FIG. 11 and FIG. 13 by the finger, etc. against the elastic force of the elastic member 172, the operation button 186 and the valve member 171 are shifted in the same direction, and the seal pad 173 is separated from the peripheral portion of the side hole 126 so that a gap is formed. Consequently, the space 110 is allowed to communicate with the outside air through the side hole 126, the cut-out of the elastic member 172 and the button-inserting holes 182 and 183, thereby allowing the air to flow therein.

In this case, the elastic member 172 is set so as to have an appropriate elasticity (rubber hardness) so that it is hardly deformed when the space 110 is brought to a reduced-pressure state by the operation of the suction plunger 105 and a force is exerted on the valve 171 to the left in FIG. 8 due to the pressure difference over the atmospheric pressure, and so that upon depression of the operation button 186 by the finger, etc., a predetermined amount of deformation is made, thereby allowing the seal pad 173 to separate from the inner face of the housing main body 121 on the periphery of the side hole 126 and to form the gap.

With respect to the constituent material of the elastic member 172, for example, the following materials are listed: various rubber materials, such as natural rubber, isoprene rubber, butadiene rubber, styrene-butadiene rubber, nitril rubber, chloroprene rubber, butyl rubber, acrylic rubber, ethylene-propylene rubber, hydrine rubber, urethane rubber, silicone rubber and fluorine-containing rubber, and various elastmers, such as styrene, polyolefin, polyvinyl-chloride, polyurethane, polyester, polyamide, polybutadiene and fluorinated elastmers. Further, various springs such as coil springs may be used as the elastic member 172.

The operation means 108 carries out the following operations: (1) a sticking operation which is made by the sticking needle 112 on the surface of a living body through the operation of the sticking plunger 103; (2) a pressure-reducing operation applied to the space 110 by the operation of the suction plunger 105; and (3) a releasing operation applied to the space 110 so as to release the reduced-pressure state to the atmospheric pressure. It is constituted by a cover (case) 181 for housing the housing main body 121, the sticking- and suction-use operation button 184, the pressing member 185 and the air-releasing operation button 186.

The above-mentioned operations (1) and (2) are carried out simultaneously, or successively in this order by the pressing of the operation button 184, and the above-mentioned operation (3) is carried out by the pressing of the operation button 186 independently from the operations.

The cover 181 also has a function for housing and maintaining the operation buttons 184 and 186. In other words, button-inserting holes 182 and 183 are formed in the cover 181 so that the operation button 184 and the operation button 186 are respectively inserted through the button-inserting hole 182 and the button-inserting hole 183.

The pressing member 185, placed on the backside of the operation button 184, is constituted by a plate-shape member made of an elastic material such as a rubber material, and is fixedly bonded from the outside of the housing 121 in a manner so as to seal the side hole 125 in an air-sealed manner. Therefore, the pressing member 185 also has a function as a sealing member.

Inside the pressing member 185 are formed a first protruding portion 185a and a second protruding portion 185b that protrude toward the inside of the side hole 125. The first protruding portion 185a contacts the first engaging section 133, and the second protruding portion 185b contacts the second engaging section 155. In this case, the height (the length of protrusion) of the first protruding portion 185a is set to be greater than the height (the length of protrusion) of the second protruding portion 185b.

The pressing member 185 is deformed in cooperation with the pressing operation of the operation button 184 in a lateral direction in FIG. 8. More specifically, when the operation button 184 is pressed to the left in FIG. 8 by the finger, etc., with the first engaging section 133 and the second engaging section 155 being engaged by the edge of the side hole 125 (see FIG. 8), the pressing member 185 is also depressed in the same direction so that the first protruding portion 185a and the second protruding portion 185b are deformed so as to protrude further into the side hole 125 (see FIGS. 9 and 10). Consequently, the first engaging section 133 and the second engaging section 155 are pressed to the left in FIGS. 9 and 10 against the elastic force of the elastic members 132 and 154, and thereby shifted. At this time, since there is a difference between the heights of the first protruding portion 185a and the second protruding portion 185b, the first engaging section 133 is first disengaged from the edge of the side hole 125, and the second engaging section 155 is then disengaged from the edge of the side hole 125, in accordance with the pressing operation of the operation button 184.

When the finger is removed from the operation button 184, the pressing member 185 and the operation button 184 are returned to their original states (states shown in FIG. 8) by the restoring force of the pressing member 185.

In the sticking tool 101A, the pressing direction of the operation button 184, that is, the operation direction in which the sticking plunger 103 is operated and allowed to stick, and the shifting direction (the sticking direction) of the sticking plunger 103 are set in different directions (directions virtually orthogonal to each other). This makes it possible to alleviate fear of the sticking operation, and also to keep unchanged the contact pressure of the tip end of the cap 122 onto the surface of a living body applied by the pressing force of the operation button 184, thereby ensuring a predetermined depth of the sticking operation.

Next, an explanation will be given of the operation of each of the parts carried out in the sticking operation of the sticking tool 101A.

[1-A] The cap 122 is removed from the housing main body 121, and the lancet 111 having the sticking needle 112 is attached to the needle holder 131 of the sticking plunger 103.

[2-A] The sticking plunger 103 with the lancet 111 attached thereto is pushed toward the base end against the elastic force of the coil spring 104 so as to allow the first engaging section 133 to engage the edge of the side hole 125. The coil spring 104 is maintained in a compressed state.

[3-A] After attaching the cap 122 to the housing main body 121, the suction plunger 105 is pushed toward the tip end against the elastic force of the coil spring 106 so as to allow the second engaging section 155 to engage the edge of the side hole 125. The coil spring 104 is maintained in an extended state.

In this state, preparation for the sticking operation onto the surface of a living body is complete (see FIG. 8).

[4-A] After the tip end of the cap 122 has been pressed onto the surface of a living body such as the finger tip with the space 110 being maintained in an air-sealed state, the operation button 184 is pressed. Upon pressing the operation button 184, the pressing member 185 is deformed so that the engagement of the first engaging section 133 with the edge of the side hole 125 is first released.

Figure 9:
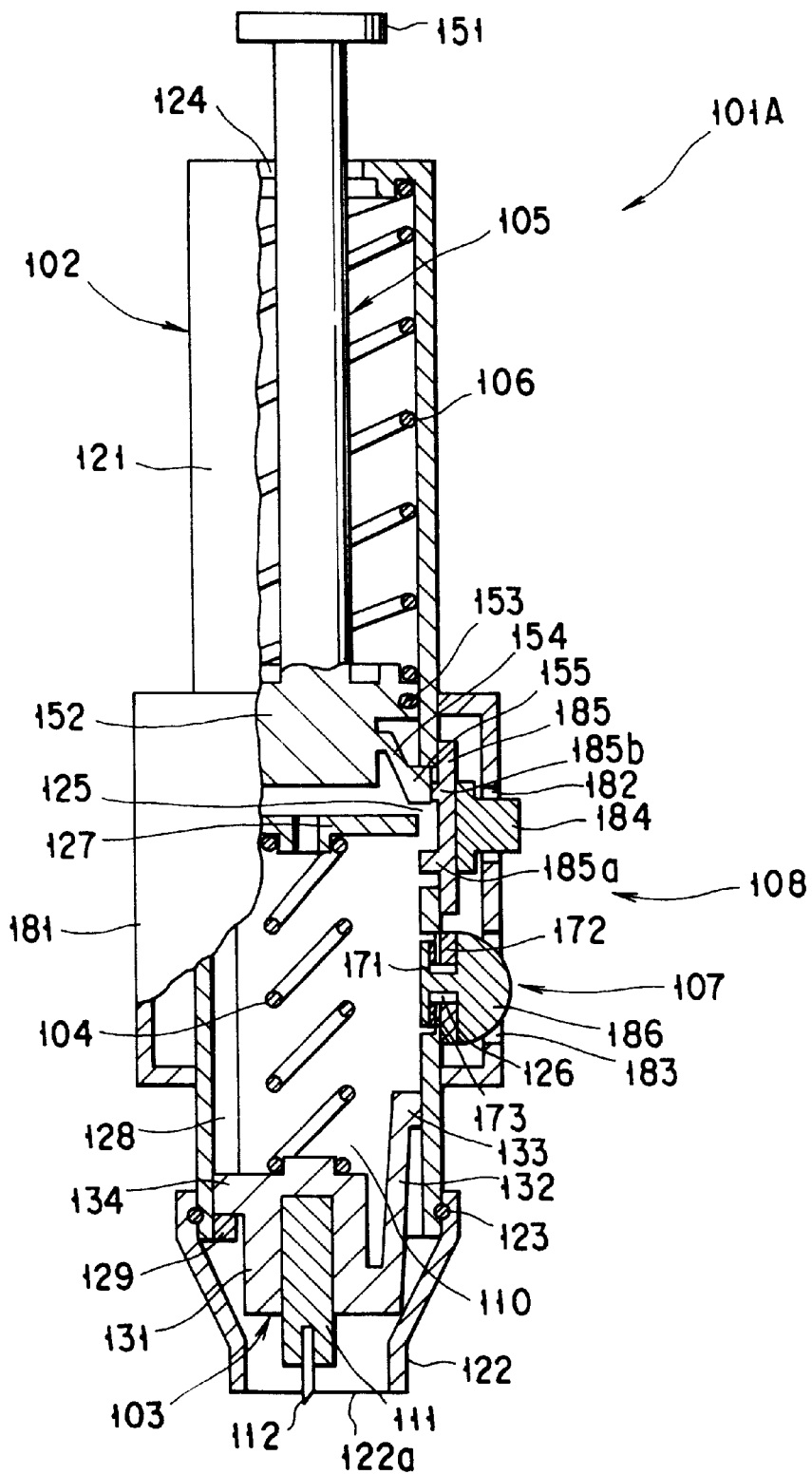
FIG. 9 is a cross-sectional view of the sticking tool of FIG. 8 that shows a state after the sticking process to the surface of the living body.

When the engagement of the first engaging section 133 has been released, the coil spring 104 which has been compressed is allowed to extend by its elastic force, thereby making the sticking plunger 103 shift toward the tip end and the sticking needle 112 protrude from the tip opening 122a so as to stick the surface of the living body (see FIG. 9).

At this time, the protruding portion 134 comes into contact with the stopper 129, thereby restricting the shift of the sticking plunger 103 toward the tip end; thus, it is possible to ensure a constant depth of the sticking operation by the sticking needle 112 onto the surface of a living body.

Figure 10:
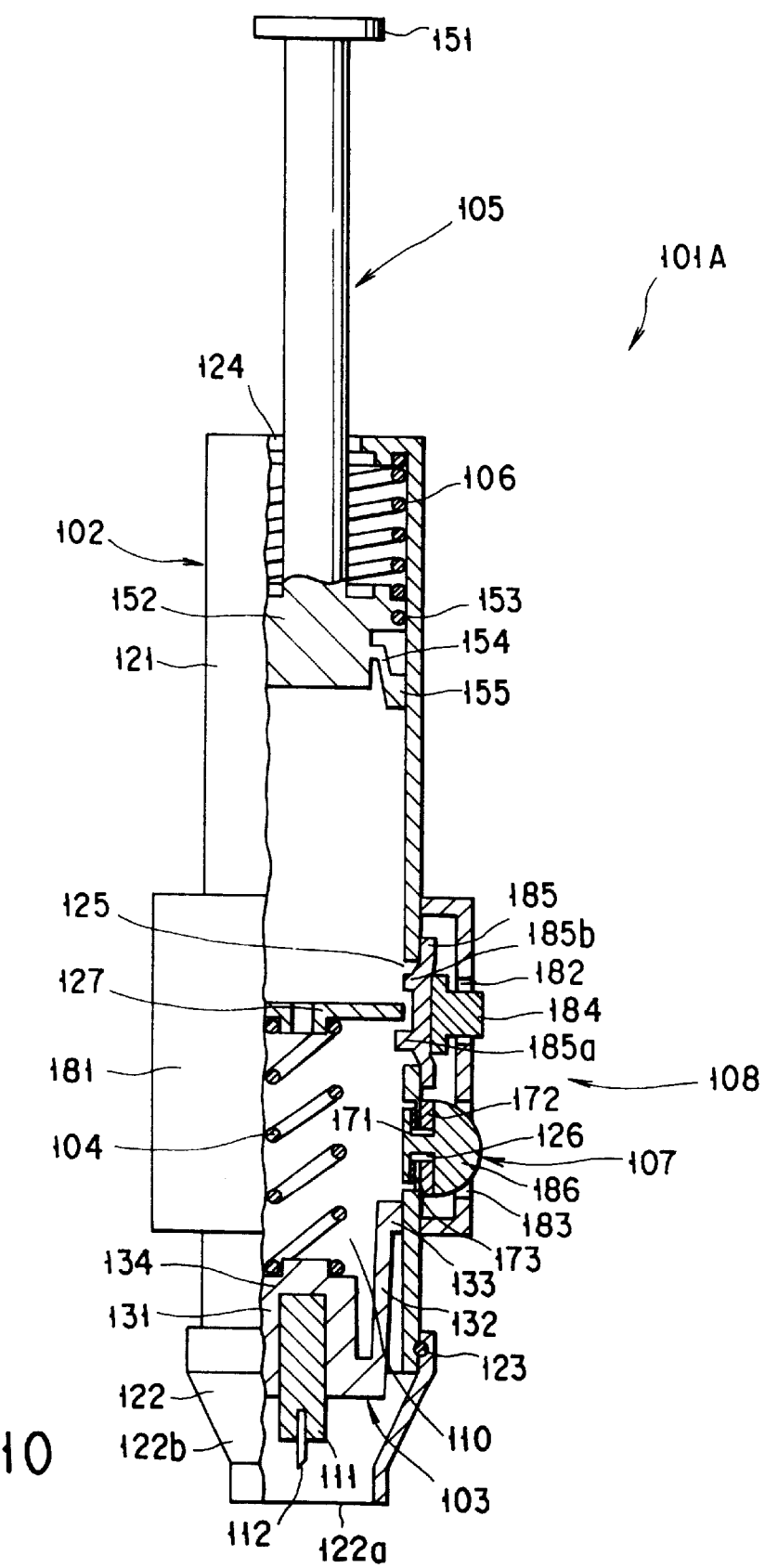
FIG. 10 is a cross-sectional view of the sticking tool of FIG. 8 in still another state.

After the sticking operation has been made by the sticking needle 112 onto the surface of a living body, the coil spring 104 is returned to its original length through damping movements, the sticking needle 112 is pulled out of the surface of the living body and stored in the housing 102 (see FIG. 10). In this manner, the sticking needle 112 is designed so as not to protrude from the tip opening 122a of the cap 122 except the sticking operation; thus, it is possible to avoid the possibility of erroneously hurting the skin, etc., and also to prevent contagion, ensuring a highly safety device.

[5-A] When, after the engagement of the first engaging section 133 has been released, the operation button 184 is further pushed, the engagement of the second engaging section 155 with the side hole 125 is released.

When the engagement of the second engaging section 155 has been released, the coil spring which has been in an extended state is allowed to shrink by its elastic force, thereby allowing the suction plunger 105 to slide toward the base end. Thus, the space 110 inside the housing 102 is increased in its volume, and gradually reduced in its pressure so that blood is sucked out through the portion that has been stuck. In other words, as compared with the case in which no suction process is applied, bleeding is further accelerated; thus, it becomes possible to ensure to suck an amount of blood required in a short time.

Here, the minimum pressure to be applied to the space 110 by the operation of the suction plunger 105 is preferably set at approximately −300 mmHg with respect to the atmospheric pressure. This makes it possible to ensure to suck an amount of blood required in a short time.

As described above, in the sticking tool 101A, the suction process (the pressure reduction in the space 110) is always started not prior to the sticking operation, but after the sticking operation; therefore, it is possible to avoid the possibility that the surface of a living body (the portion that has been stuck) swells due to the suction process and protrudes inside the tip opening 122a, causing a deeper depth of sticking beyond a preset value, that is, it becomes possible to prevent the occurrence of a greater pain.

Here, the present operation may be carried out simultaneously with the operation [4-A]. Such a simultaneous operation is available by, for example, setting the first protruding portion 185a and the second protruding section 185b to have the same heights and releasing the engagements of the first engaging section 133 and the second engaging section 155 at the same time.

[6-A] If, in the middle of the suction operation as described above, the pressure of the space 110 is not reduced sufficiently due to, for example, separation of the tip end of the cap 122 from the surface of a living body, the suction operation can be again carried out.

More specifically, the suction plunger 105 is shifted toward the tip end by pressing the handling section 151 of the suction plunger 105, the second engaging section 155 is again engaged by the edge of the side hole 125, and the tip end of the cap 122 is pressed onto the surface of the living body with the space 110 being in an air-sealed state; thereafter, the operation button 184 is pressed, thereby releasing the engagement of the second engaging section 155 so that the space 110 is brought to a reduced-pressure state so as to suck blood through the portion that has been stuck.

In the sticking tool 101A, since the suction plunger 5 and the sticking plunger 103 are independently provided, it is possible to eliminate the necessity of re-sticking the surface of a living body upon carrying out such a re-suction operation, and consequently to ensure a highly safe device. Additionally, the present operation can be repeated as many times as desired.

[7-A] After the above-mentioned operation [5-A] or [6-A], when an appropriate amount of blood is confirmed through the cap 122, the operation button 186 is pressed with the tip end of the cap 122 being in contact with the surface of the living body. This allows the air-releasing valve 107 to open based on the operational principle as described above, and the outer air flows into the space 110 through the button-inserting holes 182 and 183, the cut-out of the elastic member 172 and the side hole 126 so that the pressure of the space 110 is returned to the atmospheric pressure (see FIG. 11).

In this case, the portion of the outer air flow is considerably apart from the blood on the portion that has been stuck, and the flow of the outer air is not so rapid; therefore, no scattering occurs in the blood on the portion that has been stuck.

[8-A] When it is confirmed that the sense of being sucked has disappeared from the periphery of the portion that has been stuck on the surface of a living body and that the pressure of the space 110 has been returned to the atmospheric pressure, the sticking tool 101A is removed from the surface of a living body, and the blood on the portion that has been stuck is sampled. This sampling of blood may be carried out, for example, by directly supplying the blood onto test paper or sucking the blood through a fine tube so as to supply it to test paper.

FIGS. 14 through 17 are cross-sectional side views that respectively show another embodiment of the sticking tool of the present invention, and FIGS. 18 through 21 are cross-sectional views that respectively show a structural example of an air-releasing means.

The following description will discuss a sticking tool 101B shown in these drawings based upon distinctions from the above-mentioned sticking tool 101A, and with respect to the same operations, the description thereof is omitted. Here, in FIGS. 14 through 17, upon explanation, the upper side is referred to as "base end", and the lower side is referred to as "tip end".

The sticking tool 101B is provided with an air-releasing means which is automatically operated in accordance with the shift of the suction plunger 105 toward the base end.

The plunger 105 in the sticking tool 101B is provided with an inner space (vent path) 156 that penetrates from its base end to its tip end. Moreover, a flange 157 is formed at a position on the base end side from the air-releasing valve 109 of the suction plunger 105, and the tip end of the coil spring 106 is secured to the flange 157.

The air-releasing valve (air-releasing means) 109 is installed in the suction plunger 105. As illustrated in FIGS. 18 through 21, the air-releasing valve 109 is constituted by an operation member 191 having an inverted letter C-shape when viewed from the top, a seal member 192 secured to one end of the operation member 191 and a tube body 193 having a vent inlet 193d. A head portion 191a is attached to the other end of the operation member 191, and a slanting slope 191b is formed in the head portion 191a.

Figure 18:
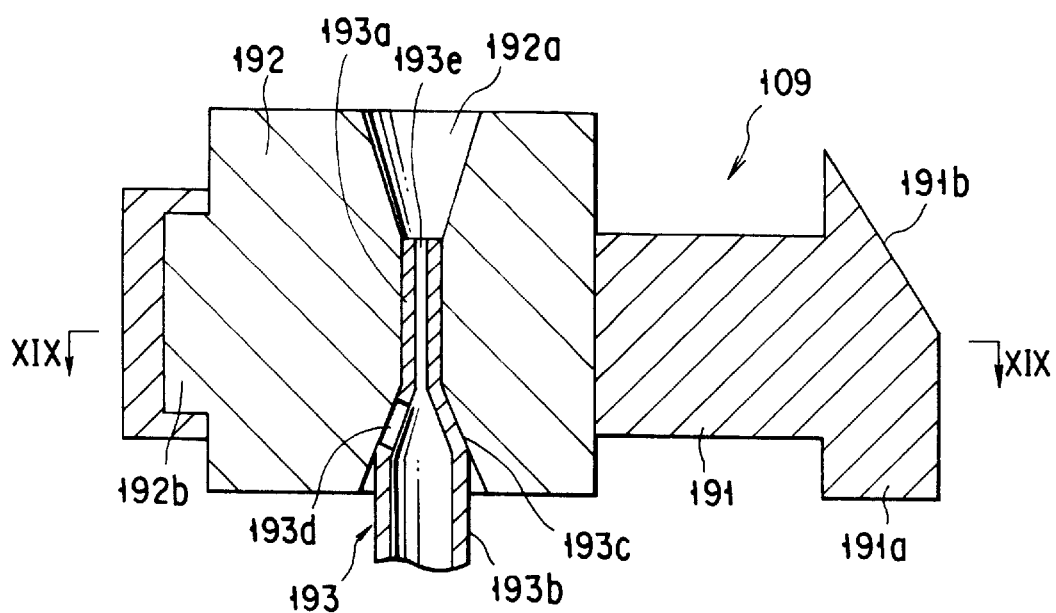
FIG. 18 is a cross-sectional view showing the structure of an air-releasing means in the sticking tool as shown in FIGS. 14 to 17.

The seal member 192 is made of an elastic material as described earlier, and a vent path 192a having a narrow-diameter section is formed in the center thereof. As illustrated in FIG. 18, the upper end of the vent path 192a communicates with an inner space 156 formed in the suction plunger 105 on the base-end side from the flange 157.

Furthermore, a fitting section 192b is formed in the seal member 192, and the fitting section 192b is fitted to one end of the operation member 191 and fixedly bonded thereto. The portion of the seal member 192, which is opposite to the fitting section 192b with the vent path 192a located in between, is secured to the suction plunger 105, and is maintained in an immovable state against the shift of the operation member 191.

The tube body 193, which is inserted into the vent path 192a, is provided with a small-diameter section 193a and a large-diameter section 193b, and a taper section 193c that connects these sections. A vent opening 193d which allows the inside and outside of the tube body 193 to communicate with each other is formed in the taper section 193c. The small-diameter section 193a and the taper section 193c of the tube body 193 closely contact the inner face of the vent path 192a with the seal member 192 sandwiched along all circumferential area thereof (see FIG. 18 and FIG. 19).

The end of the large-diameter section 193b of the tube body 193 is inserted into the inner space 156 formed inside the gasket 152 so that the inside of the tube body 193 and the inner space 156 are allowed to communicate with each other.

A fine flow-path 193e for ensuring a fine amount of ventilation is formed inside the small-diameter section 193a of the tube body 193. The fine flow-path 193e communicates with the vent path 192a.

Here, with respect to the constituent material of the tube body 193, any of hard materials such as a hard resin and a metal material, soft materials such as a soft resin and elastic materials as described earlier, may be applied; however, it is preferable to use hard or soft resin materials.

Next, an explanation will be given of the operation of the air-releasing valve 109.

Figure 19:
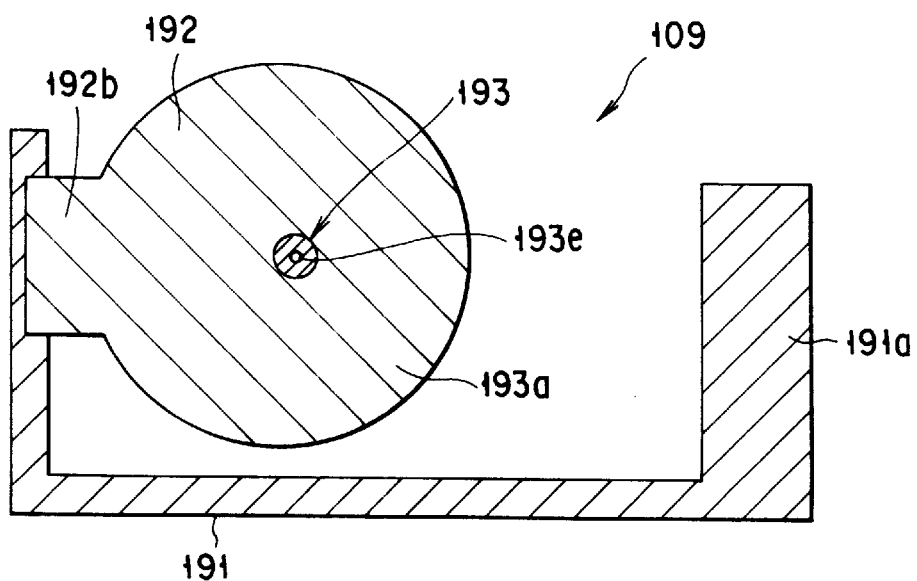
FIG. 19 is a cross-sectional view taken along the line XIX—XIX.

As illustrated in FIG. 18 and FIG. 19, in a state in which the head section 191a is not subjected to a pressing force, the small-diameter section 193a and the taper section 193c of the tube body 193 closely contact the inner face of the vent path 192a with the seal member 192 sandwiched along all the circumferential area thereof. This blocks the vent opening 193d, making a state in which the inner spaces 56 are virtually shielded from the air flow (a state in which the air-releasing valve 109 has been closed). Here, although the inner spaces 156 at the respective ends of the air-releasing valve 109 communicate with each other through the fine flow-path 193e, this hardly gives any effect in bringing the space 110 to a reduced-pressure state since the amount of air allowed to pass through it is very small.

Figure 20:
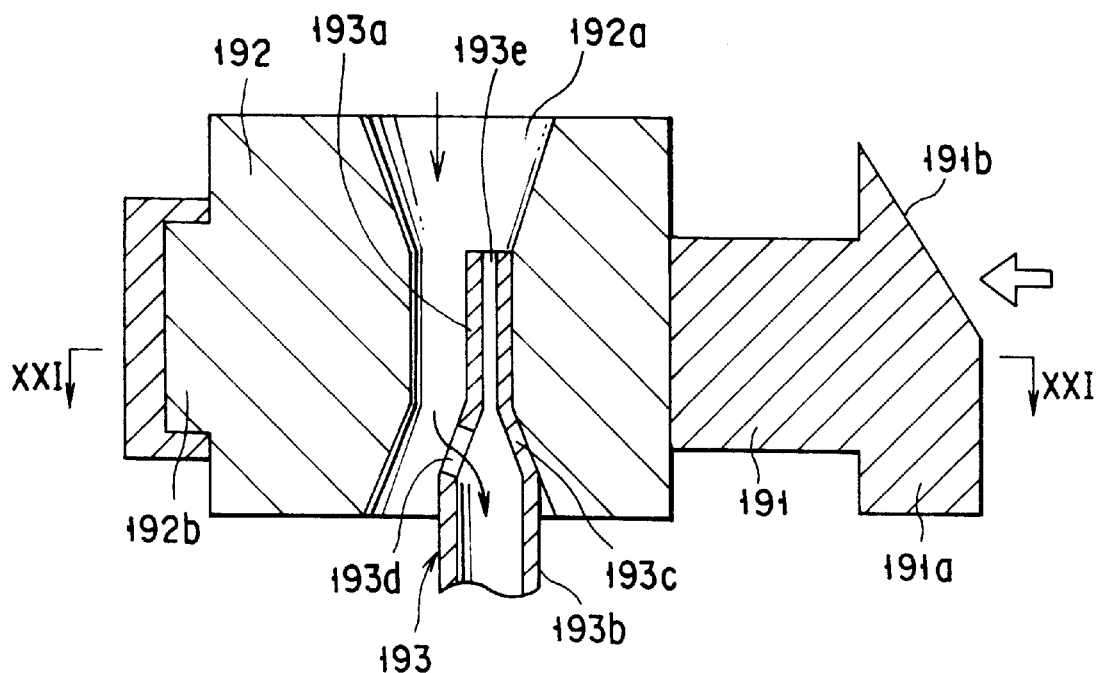
FIG. 20 is a cross-sectional view showing the air-releasing means in a different state.
Figure 21:
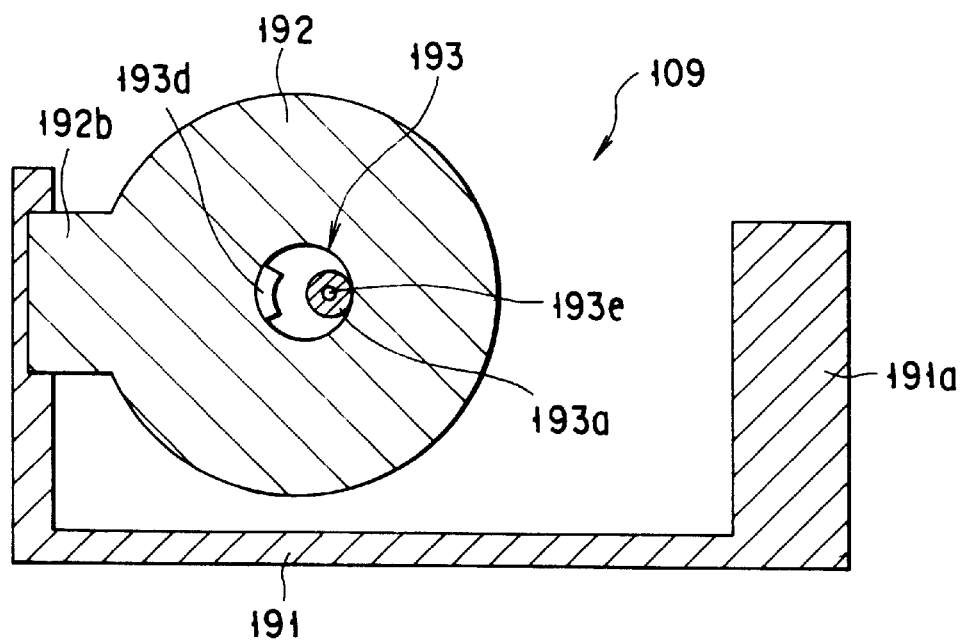
FIG. 21 is a cross-sectional view taken along the line XXI—XXI.

As illustrated in FIG. 20 and FIG. 21, when a pressing force is applied to the head section 191a to the left in the drawing, the seal member 192 is pulled in the same direction at its fitting section 192b, and deformed so that the vent path 193a is expanded. Thus, a gap is formed between the small-diameter section 193a and the taper section 193c of the tube body 193 and the inner face of the vent path 192a, thereby making a state in which the vent opening 193d is opened (a state in which the air-releasing valve 109 is opened). Thus, the inner spaces 156 at the respective ends of the air-releasing valve 109 are allowed to communicate with each other through the vent path 193a, the vent opening 193d and the inside of the tube body 193 so that air flow is available. When the air-releasing valve 109 is opened in a reduced-pressure state of the space 110, air flows into the space 110 through paths indicated by arrows in FIG. 20.

When the pressing force, applied to the head section 191a, is removed, the seal member 192 is returned to its original shape as shown in FIG. 18 and FIG. 19 by its restoring force, resulting in a state in which the air-releasing valve 109 is again closed.

The air-releasing valve 109 also serves as a relief valve which, upon having a pressurized state in the space 110 due to the shifting operation of the suction plunger 105 toward the tip end, releases air corresponding to the excessive pressure. In other words, when the space 110 is brought into a pressurized state with the air-releasing valve 109 being closed (a state shown in FIG. 18 and FIG. 19), the air inside the space 110 is externally released through the fine flow-path 193e of the tube body 193 little by little.

A slanting face (cam face) 121a, which engages the slanting face 191b of the head section 191a, is formed in the inner face on the base-end side of the housing main body 121. When the suction plunger 105 is shifted toward the base end and the slanting face 191b of the head section 191a comes into contact with the slanting face 121a, and slides thereon (see FIG. 16), the slanting face 191b is pushed toward the center axis (to the left in FIG. 16) of the suction plunger 105, the operation member 191 is shifted in the same direction, and the air-releasing valve 109 is opened based upon the operational principle as described earlier.

Moreover, a step-gap section 121b is formed in the inner face on the base-end side of the housing main body 121, which is the side opposite to the slanting face 121a. The step-gap section 121b engages the outer circumferential portion on the base-end side of the gasket 152 so as to restrict the shift of the suction plunger 105 toward the base end.

The opening of the air-releasing valve 109, which is made when the slanting face 191b passes through the slanting face 121a, takes place immediately before the gasket 152 is engaged by the step-gap section 121b, that is, immediately before the suction plunger 105 has arrived at the limit position of shift on the base-end side.

The time that is taken from the release of the engaging section 155 from the edge of the side hole 125 to the opening of the air-releasing valve 109 is set as a time period that sufficiently allows an amount of blood required to be sucked through the portion that has been stuck by the sticking needle 112; and, for example, this is preferably set in the range of 3 to 10 seconds. This time can be set appropriately by selecting factors, such as the spring elasticity of the coil spring 106, the sliding resistance of the seal ring 153 against the inner face of the housing main body 121, the shift stroke of the suction plunger 105 and the installation position of the slanting face 121a. For example, the time can also be adjusted by exchanging the coil spring 106 and/or the seal ring 153.

A stopper 129a with which the tip face of the needle holder 131 comes into contact is formed in the inner face of the tip end of the housing main body 121. The stopper 129a is secured to the inner surface of the housing main body 121, for example, by means of threads, and can be adjusted in its position in the length direction with respect to the housing main body 121 by the amount of revolutions of the threads. In this manner, the amount of protrusion of the sticking needle 112, that is, the depth of sticking into the surface of a living body, can be adjusted depending on individual differences in the person whose blood is to be sampled (the subject) and differences in the portion to be stuck.

Here, with respect to the threading structure (not shown) of the stopper 129a to the housing main body 121, for example, the gear structure of a micrometer may be adopted. Moreover, it is preferable to adjust the depth of sticking of the sticking needle 112 by the unit of 0.1 mm or in a stepless manner.

Next, an explanation will be given of the operation of each of the parts in carrying out the sticking operation by using the sticking tool 101B.

[1-B] The cap 122 is removed from the housing main body 101B, and the lancet 111 having the sticking needle 12 is attached to the needle holder 131 of the sticking plunger 103.

Moreover, the position of the stopper 129a in the length direction with respect to the housing main body is adjusted so that the depth of sticking is appropriately set in accordance with individual differences in the person whose blood to be sample and differences in the portion to be stuck. With respect to the standard of the setting of the depth of sticking, for example, it may be set at a depth of sticking that allows to obtain a minimum amount of blood required for measuring the blood-sugar value. Thus, it is possible to reduce a pain accompanying the sticking operation to a minimum level required.

Here, once the position of the stopper 129a has been set, it is not necessary to reset it every time a blood sampling is carried out; therefore, no time-consuming process is required in the operation.

[2-B] the same as the aforementioned process [2-A].

Figure 14:
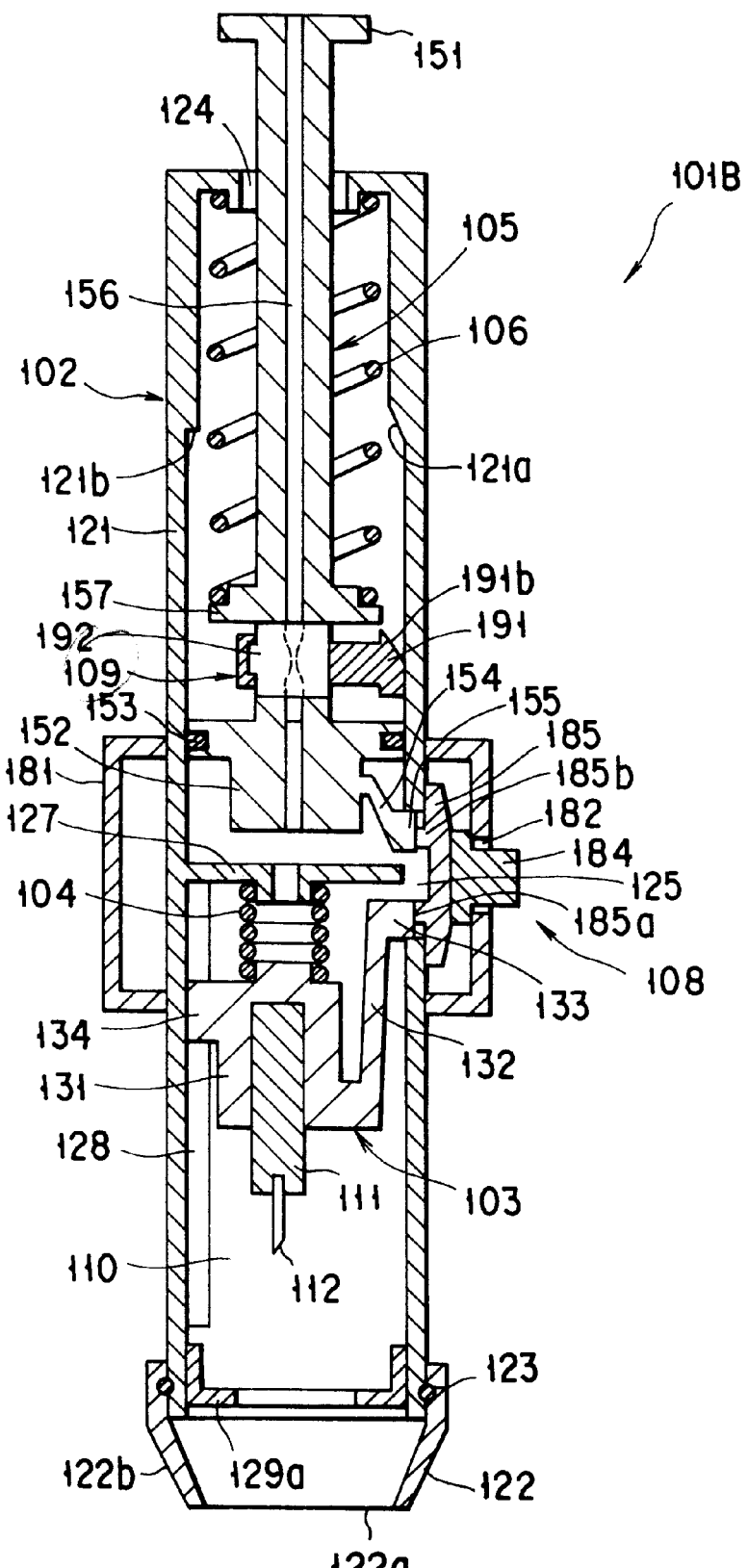
FIGS. 14 to 17 are cross-sectional views showing, in different states, another embodiment of a sticking tool which can be suitably used in a body-fluid inspection device of the present invention.

[3-B] the same as the aforementioned process [3-A] (see FIG. 14).

Figure 15:
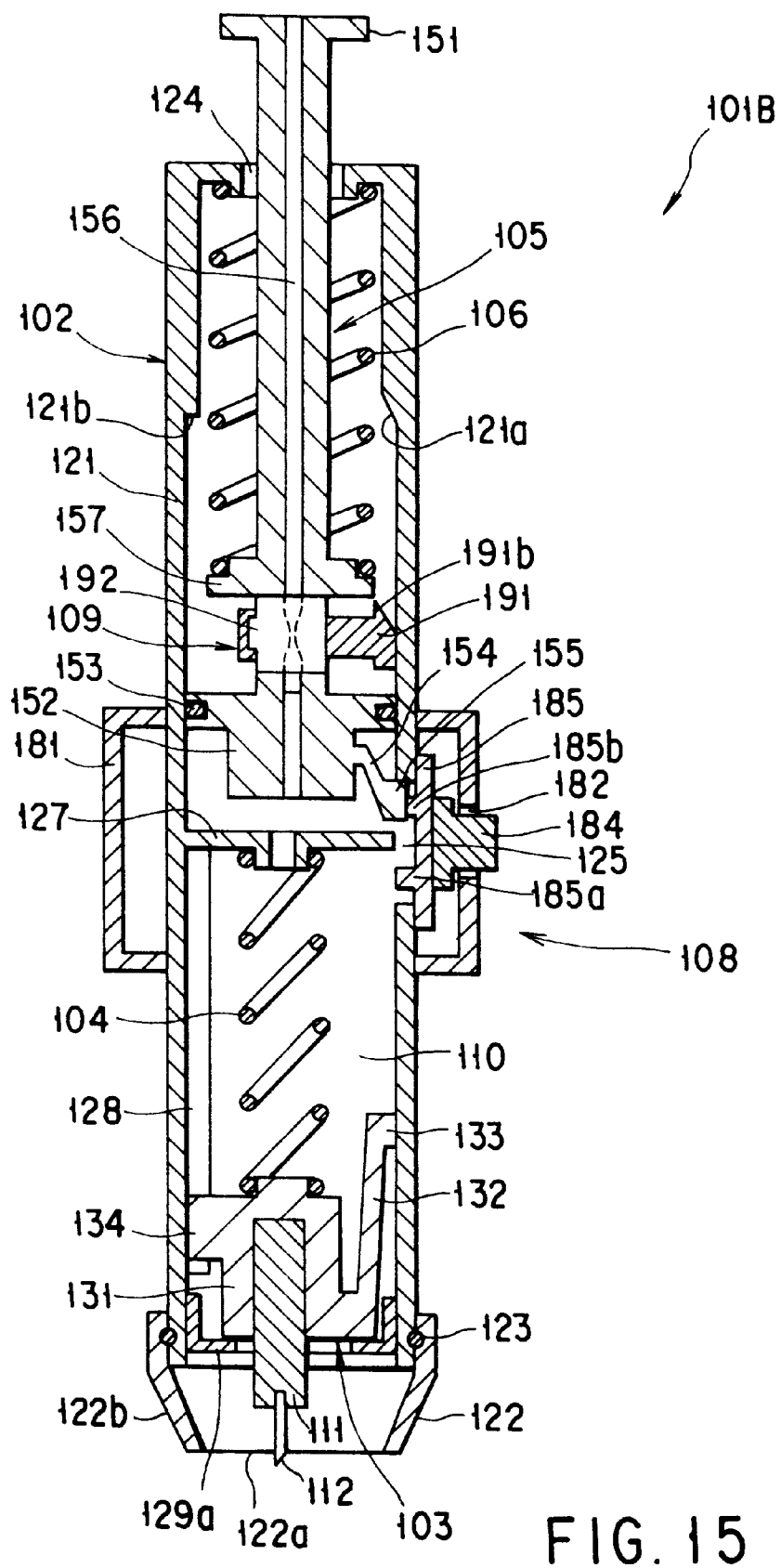

[4-B] the same as the aforementioned process [4-A] (see FIG. 15).

Figure 16:
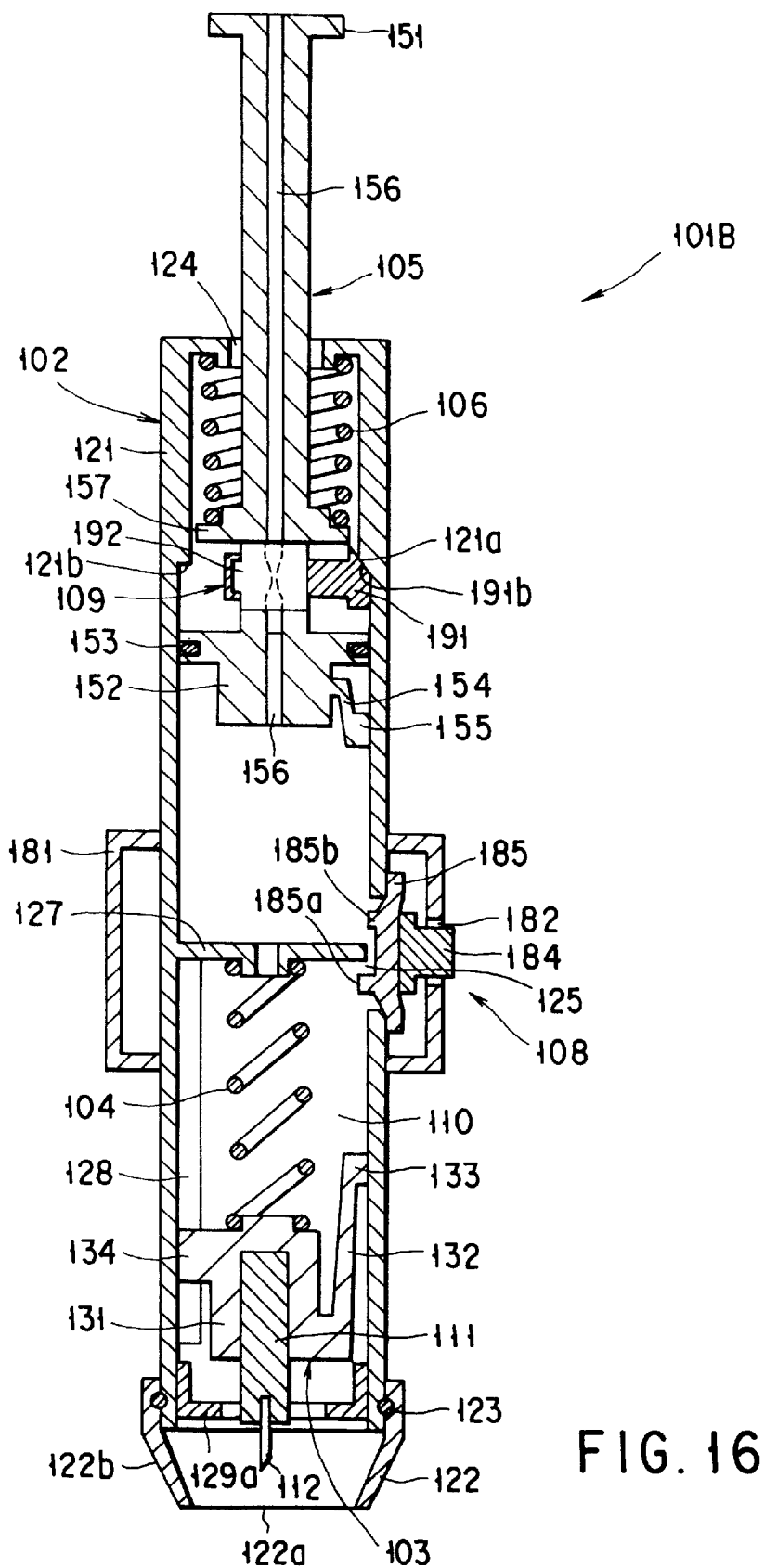
Figure 17:
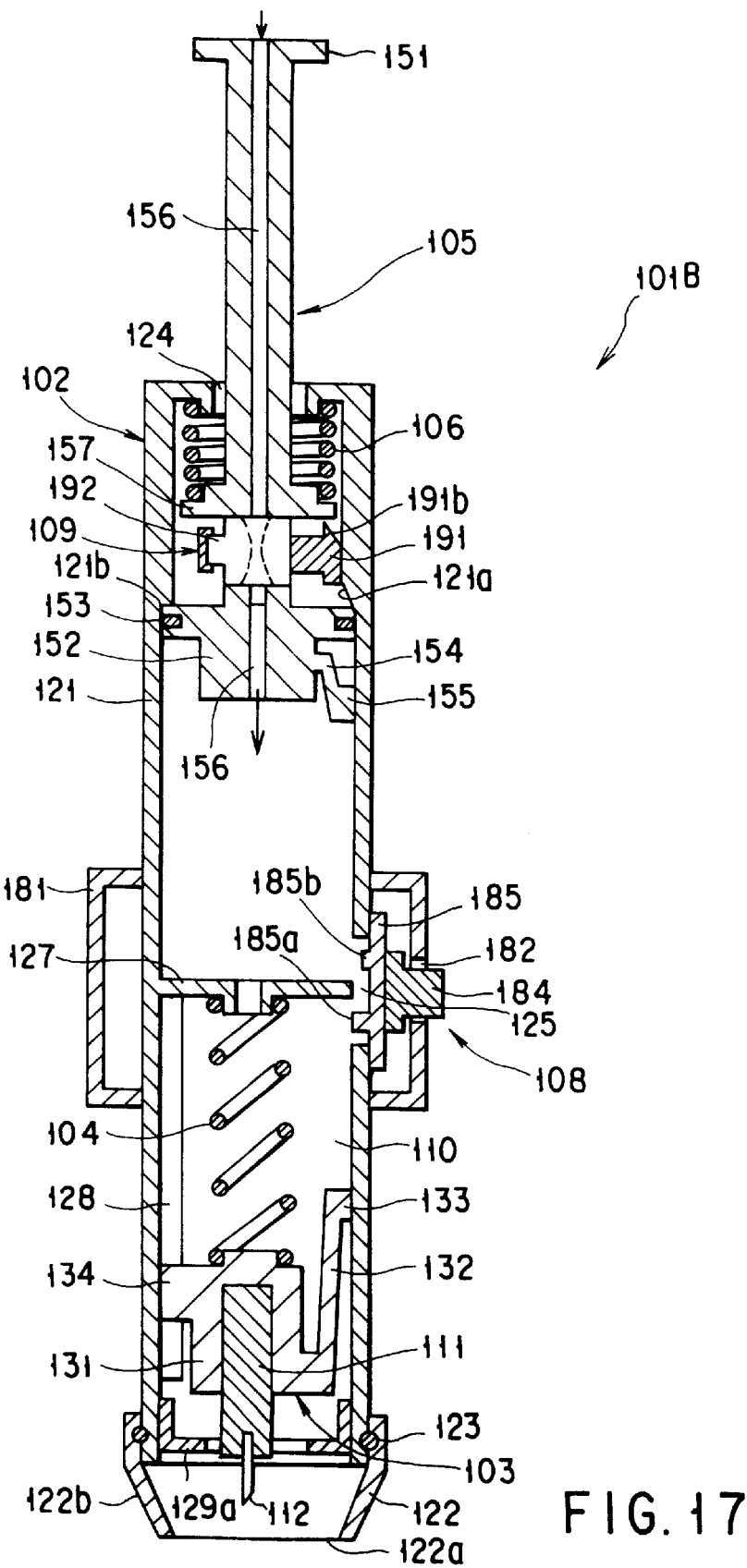

[5-B] the same as the aforementioned process [5-A] (see FIG. 16).

[6-B] When the suction plunger 105 is shifted toward the base end and the slanting face 191b comes into contact with the slanting face 121a, and is allowed to slide thereon (see FIG. 16), the operation member 191 is shifted in the same direction so that the air-releasing valve 109 is opened based on the operational principle as described earlier. Thus, the outer air flows into the space 110 through the inner spaces 156, thereby allowing the pressure of the space 110 to return to the atmospheric pressure (see FIG. 17).

In this case, the portion of the outer air flow is considerably apart from the blood on the portion that has been stuck, and the flow of the outer air is not so rapid; therefore, no scattering occurs in the blood on the portion that has been stuck.

[7-B] If, in the middle of the suction operation as described above, the pressure of the space 110 is not reduced sufficiently due to, for example, separation of the tip end of the cap 122 from the surface of a living body, the suction operation can be again carried out.

More specifically, the suction plunger 105 is shifted toward the tip end by pressing the handling section 151 of the suction plunger 105, the second engaging section 155 is again engaged by the edge of the side hole 125, and the tip end of the cap 122 is pressed onto the surface of the living body with the space 110 being in an air-sealed state in the same manner as described earlier; thereafter, the operation button 184 is pressed, thereby releasing the engagement of the second engaging section 155 so that the space 110 is brought to a reduced-pressure state so as to suck blood through the portion that has been stuck, and the pressure of the space 110 is automatically returned to the atmospheric pressure.

Here, when the suction plunger 105 is pressed and shifted toward the tip end with the tip end of the cap 122 being pressed onto the surface of a living body, the pressure in the space 110 is raised from the atmospheric pressure, making a pressurized state in the space 110, since the space 110 is tightly sealed. However, since the air-releasing valve 109 also serves as a relief valve as described earlier, air corresponding to the excessive pressure is externally released through the fine flow-path 193e of the tube body 193.

In the sticking tool 101B, since the suction plunger 105 and the sticking plunger 103 are independently provided, it is possible to eliminate the necessity of re-sticking the surface of a living body upon carrying out such a re-suction operation, and consequently to ensure a highly safe device.

Additionally, the present operation can be repeated as many times as desired.

[8-B] the same as the aforementioned process [8-A].

In the sticking tool 101B, after the suction process, the pressure inside the housing 102 is automatically returned to the atmospheric pressure, without the need for the operation of the person whose blood is to be sampled (the subject), etc.; therefore, it is possible to reduce dispersions in the amount of sampled blood resulting from an erroneous judgement on the timing for the return to the atmospheric pressure, and also to prevent scattering of blood due to the fact that the operator forgot to return the pressure to the atmospheric pressure. Consequently, a more appropriate blood inspection is available.

FIGS. 22 through 25 are cross-sectional side views that respectively show another embodiment of the sticking tool of the present invention.

The following description will discuss a sticking tool 101C shown in these drawings based upon distinctions from the above-mentioned sticking tool 101A, and with respect to the same operations, the description thereof is omitted. Here, in FIGS. 22 through 25, upon explanation, the upper side is referred to as "base end", and the lower side is referred to as "tip end".

Merely by pressing the operation button 184, the sticking tool 101C makes it possible to carry out the sticking operation by the use of the sticking needle 112, the suction operation (reduction of the pressure in the space 110) and the releasing operation of the space 110 to the atmospheric pressure in this order.

A branch path 194, which communicates with the space 110, is formed in the side of the housing main body 121. The branch path 194 is housed in the cover 181. The air-releasing valve (air-releasing means) 109 which is the same as that of the sticking tool 101B is installed at the end of the branch path 194 in a manner so as to seal (shield) the inside of the branch path 194.

Moreover, a lever 184a is attached to the operation button 184 in a manner so as to stick in a direction orthogonal to the shifting direction of the operation button 184. When the operation button 184 is pressed and shifted to the left in FIG. 22, the engagements of the first engaging section 133 and the second engaging section 155 are successively removed, and the lever 184a is then allowed to contact the head section 191a, thereby pressing the pressing member 191 in the same direction so that the air-releasing valve 109 is opened based on the operational principle as described earlier (see FIG. 25).

Furthermore, the sticking tool 101C is provided with the same stopper 129a as described earlier on the inside of the tip end of the housing main body 121.

Next, an explanation will be given of the operation of each of the parts in carrying out the sticking operation by using the sticking tool 101C.

[1-C] the same as the aforementioned process [2-B].

[2-C] the same as the aforementioned process [2-A].

Figure 22:
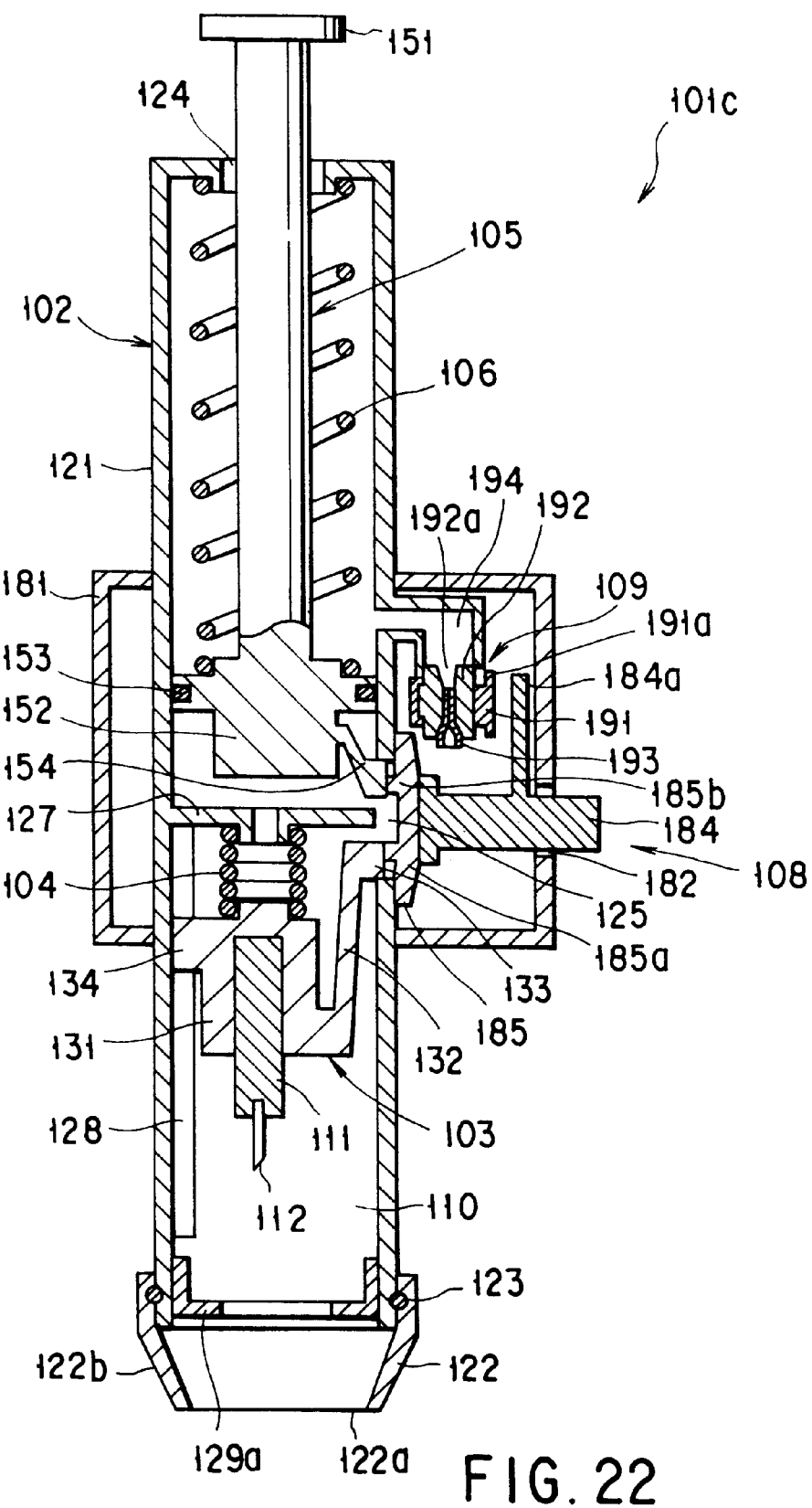
FIGS. 22 to 25 are cross-sectional views showing, in different states, still another embodiment of a sticking tool which can be suitably used in a body-fluid inspection device of the present invention.

[3-C] the same as the aforementioned process [3-A] (see FIG. 22).

Figure 23:
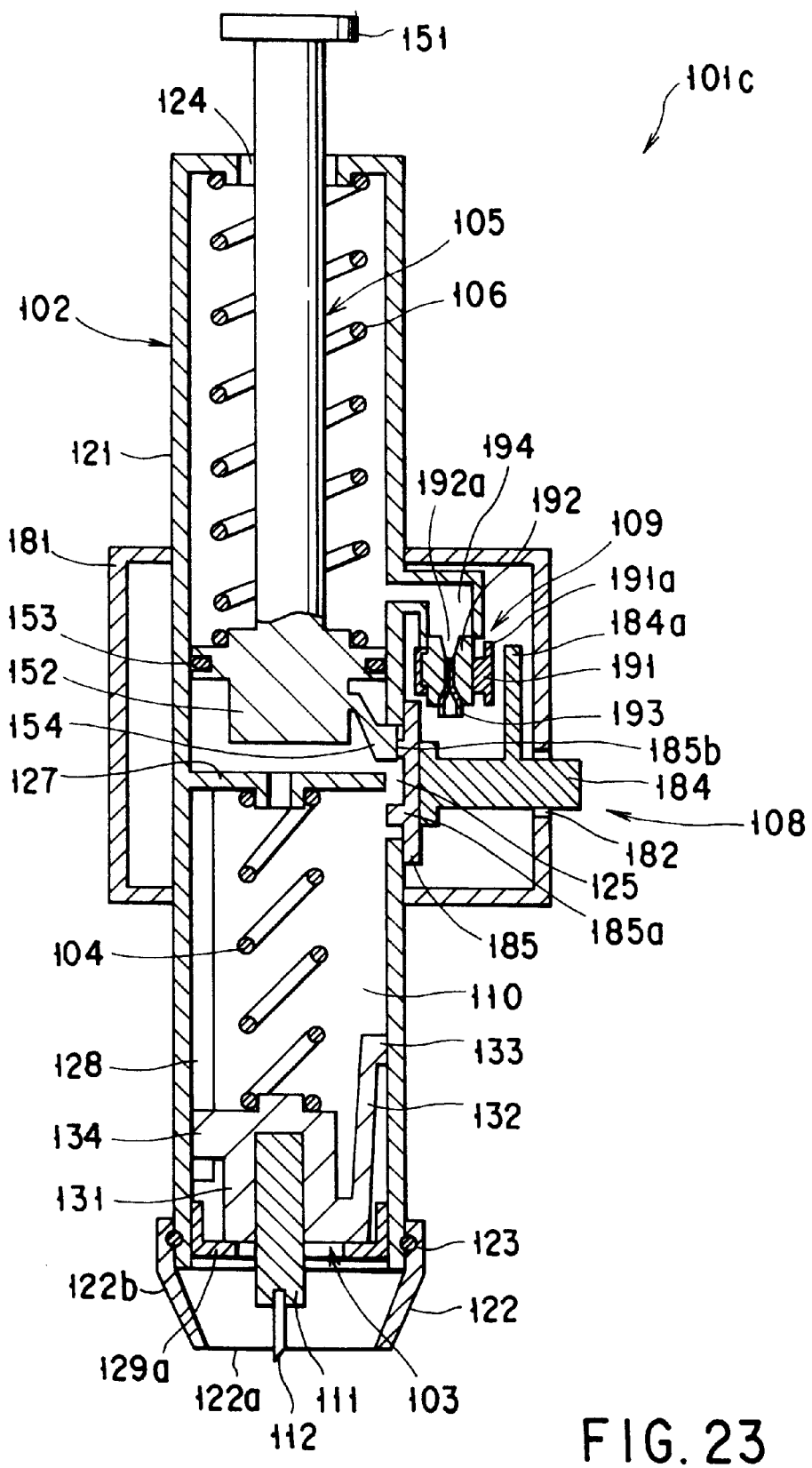

[4-C] the same as the aforementioned process [4-A] (see FIG. 23).

Figure 24:
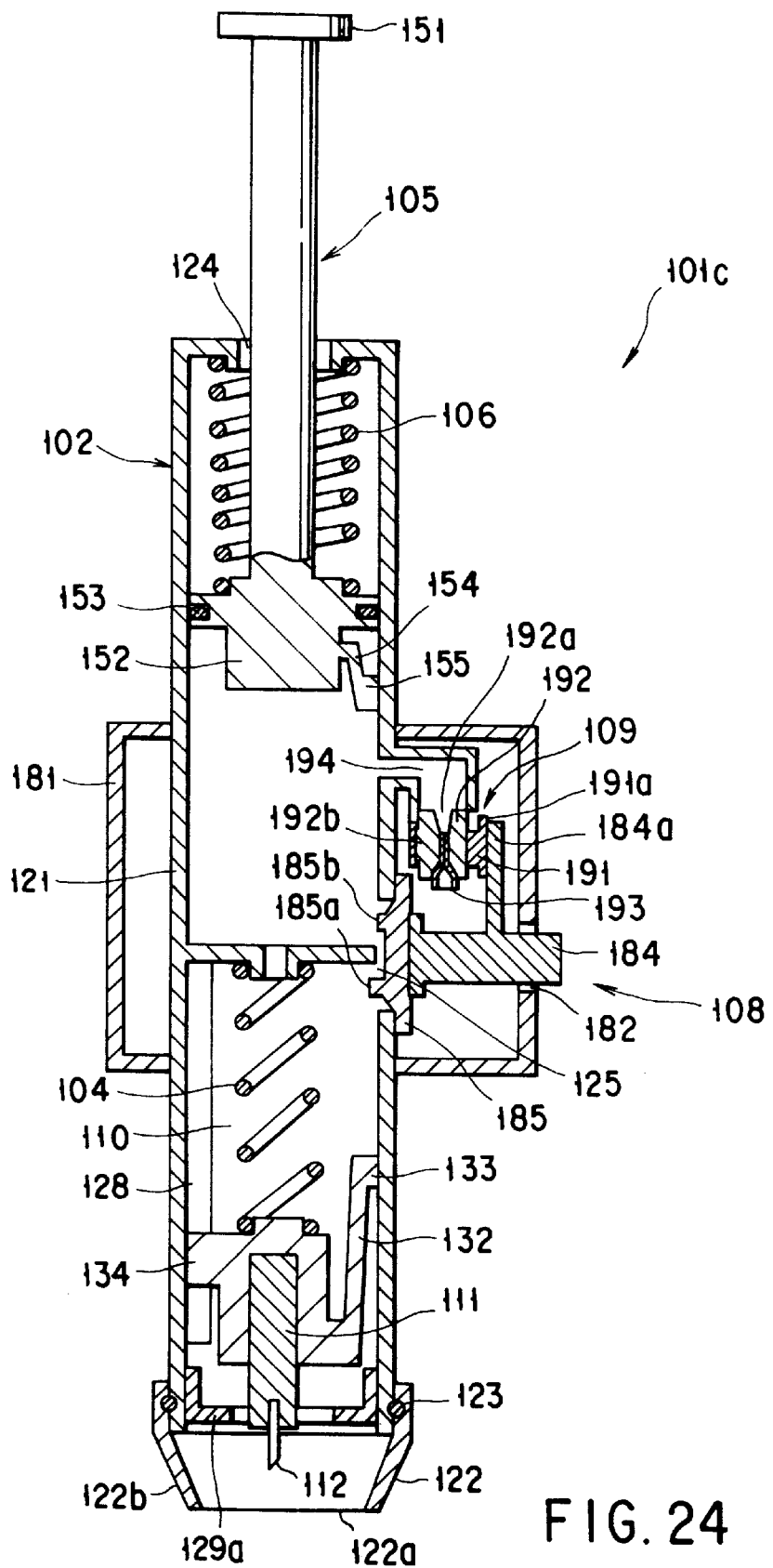

[5-C] the same as the aforementioned process [5-A] (see FIG. 24).

[6-C] the same as the aforementioned process [6-A].

Figure 25:
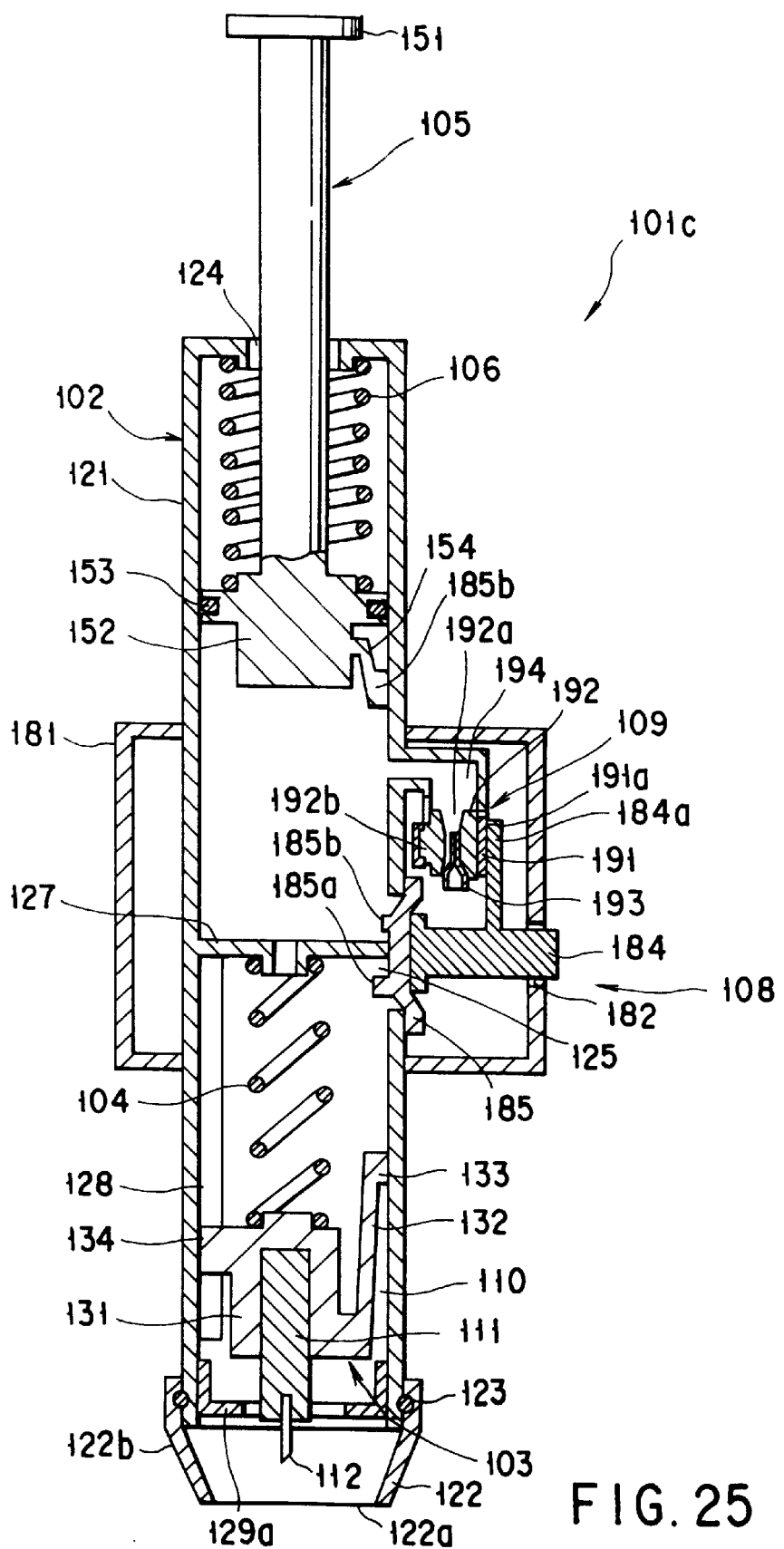

[7-C] After the above-mentioned process [5-C] or [5-C], when an appropriate amount of blood is confirmed through the cap 122, the operation button 184 is further pressed to the left in FIG. 25, with the tip end of the cap 122 being in contact with the surface of the living body. This allows the lever 184a to contact the head section 191a, and the operation member 191 is pressed and shifted in the same direction so that the air-releasing valve 109 is opened based on the operational principle as described earlier. Thus, the outer air flows into the space 110 through the button-inserting hole 182, the air-releasing valve 109 and the branch path 194 so that the pressure of the space 110 is returned to the atmospheric pressure (see FIG. 25).

In this case, the portion of the outer air flow is considerably apart from the blood on the portion that has been stuck, and the flow of the outer air is not so rapid; therefore, no scattering occurs in the blood on the portion that has been stuck.

[8-C] the same as the aforementioned process [8-A].

In the sticking tool 101C, merely by pressing the operation button 184, it is possible to carry out the sticking operation by the use of the sticking needle 112, the suction operation and reduction of the pressure in the space 110 and the releasing operation of the space 110 to the atmospheric pressure in this order; this ensures superior operability.

The above descriptions have discussed the sticking tools of the present invention based upon the respective embodiments illustrated by the drawings, however, the present invention is not intended to be limited by these, and, for example, the structure of each part may be replaced by any structure capable of achieving the same functions.

Moreover, the above descriptions have discussed the case in which blood is sampled; however, the sticking tools of the present invention are not intended to be limited thereby. For example, they may be used for sampling body fluids other than blood, such as inter-organ fluids, and the application is not particularly limited.

In accordance with the sticking tools of the present invention that have been discussed referring to FIGS. 8 through 25, the suction process is carried out on the periphery of the portion that has been stuck so as to accelerate the flow of body fluids (bleeding); therefore, it is possible to ensure to obtain an amount of body fluids required for an inspection, etc. quickly, even if only a shallow sticking is made so as to reduce pain.

Moreover, the mechanism for releasing the inside of the housing so as to return the pressure to the atmospheric pressure after the suction process is provided; therefore, it is possible to prevent scattering of the body fluids due to a rapid air flow occurring in the proximity of the portion that has been stuck. In particular, since such an air-releasing operation is carried out without the need for the shift of the sticking needle (coming close to the surface of a living body), it is possible to prevent an erroneous sticking recurring on the surface of the living body, and consequently to provide a highly safe device.

Furthermore, the sticking operation and the suction operation are carried out in this order or at the same time, and the air-releasing operation is then carried out successively. These operations are extremely simple, and it is possible to provide an appropriate depth of sticking by the sticking needle, and consequently to ensure an amount of body fluids required merely by giving a minimum pain.

In particular, in the case when the mechanism for adjusting the depth of sticking is installed, the depth of sticking can be appropriately adjusted depending on various conditions, such as individual differences and differences in the portion to be stuck, and every time a body-fluid sampling (blood sampling) operation is performed, a constant depth of sticking is provided.

Moreover, preparation operations prior to use, that is, operations for setting the sticking plunger and suction plunger in an operative state, are simple and easy; this is advantageous when the device is used regularly or repeatedly.

Furthermore, since the sticking needle is designed not to protrude from the tip opening except for the sticking operation, it is possible to prevent accidents such as an erroneous sticking; this ensures a highly safe device. In addition, since the sticking needle is not directly visible, it is possible to alleviate fear of sticking.

In the case when the sticking direction of the sticking needle and the operation direction of the sticking operation are made different from each other, the force applied by the operation upon sticking is not exerted on the surface of a living body; therefore, it is possible to ensure a more stable sticking operation, to achieve a depth of sticking as has been preset, and also to alleviate fear of sticking.

As described above, the sticking tool of the present invention is suitable for cases in which the patient measures his or her own blood-sugar value, etc.

Moreover, the sticking tool of the present invention has a simple structure and is suitable for mass production.

Referring to FIGS. 26 through 39, the following description will discuss still another embodiment of the sticking tool of the present invention in detail.

Figure 26:
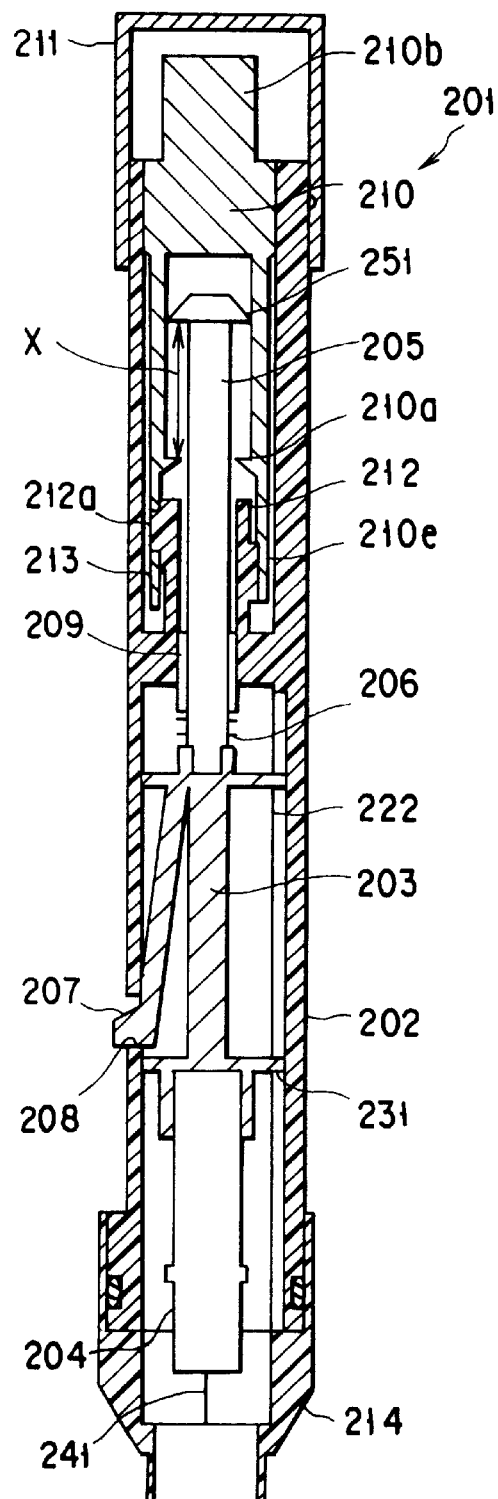
FIG. 26 is a cross-sectional view showing still another embodiment of a sticking tool which can be suitably used in a body-fluid inspection device of the present invention.
Figure 28:
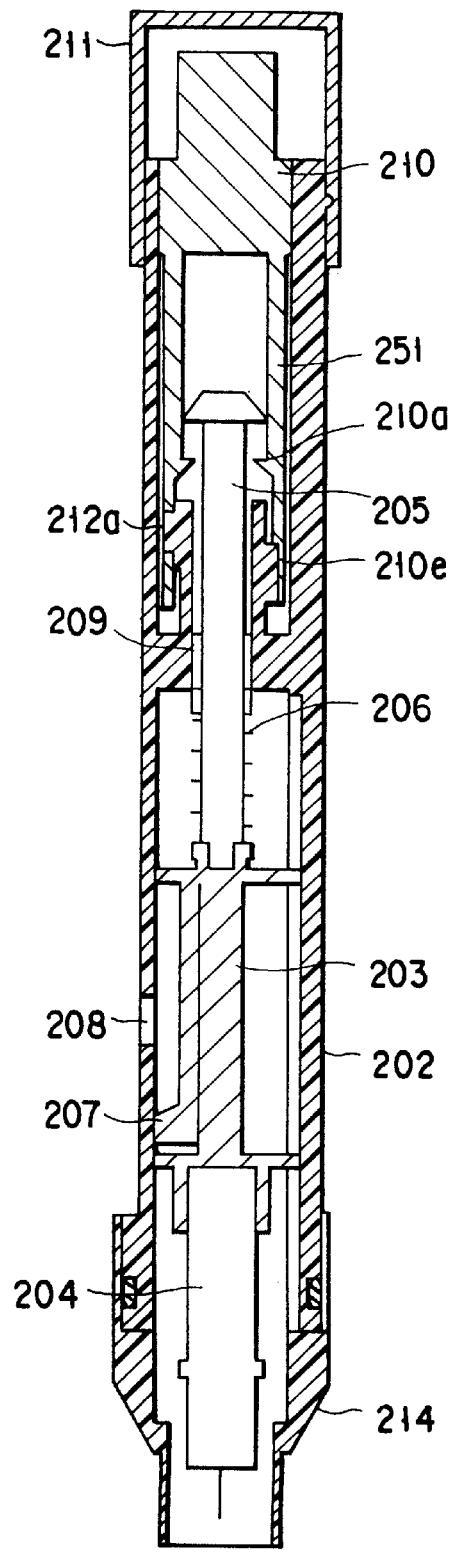
FIG. 28 is a cross-sectional view showing the sticking tool of FIG. 26 after the sticking.
Figure 27:
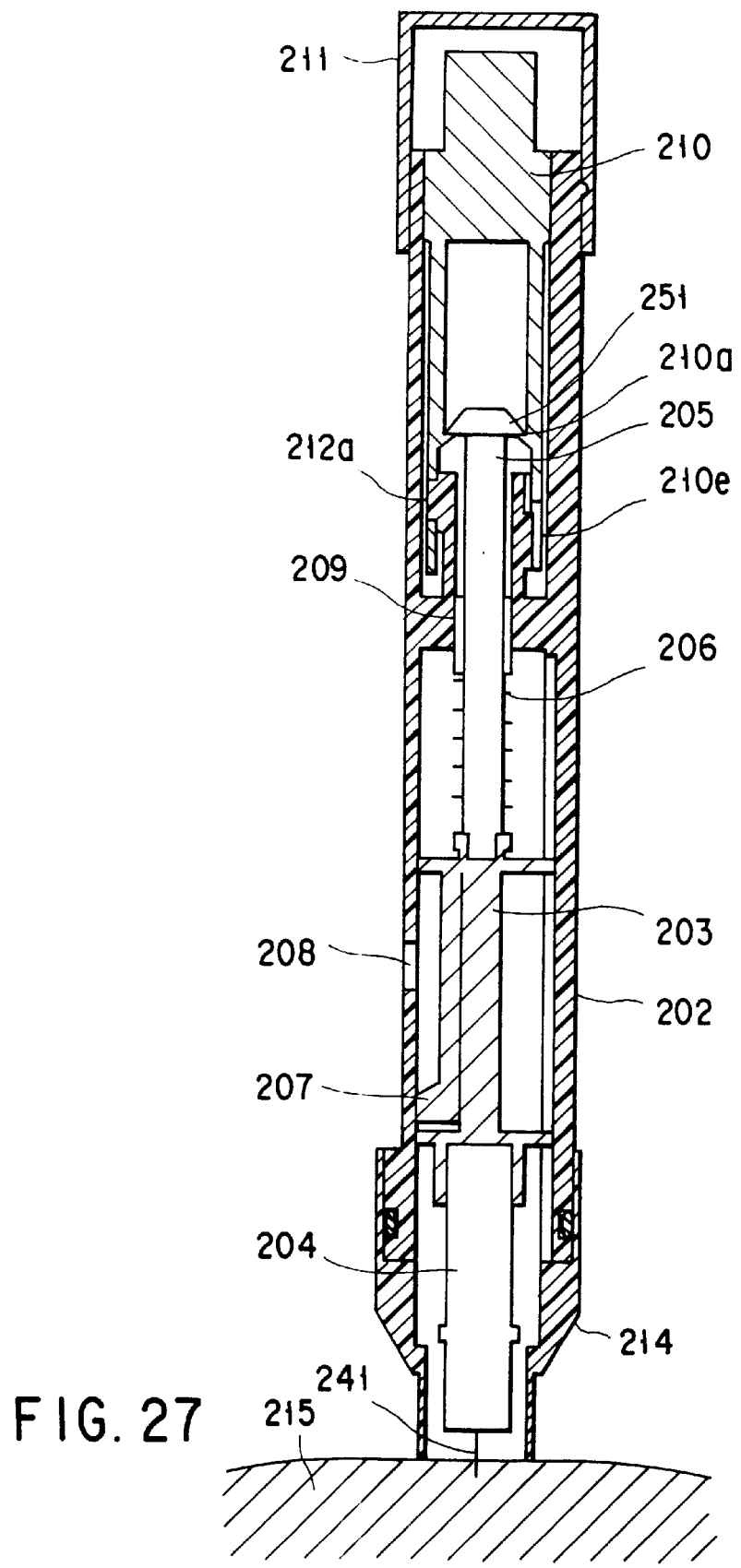
FIG. 27 is a cross-sectional view showing a state in which the sticking tool of FIG. 26 sticks a surface of a living body.
Figure 29:
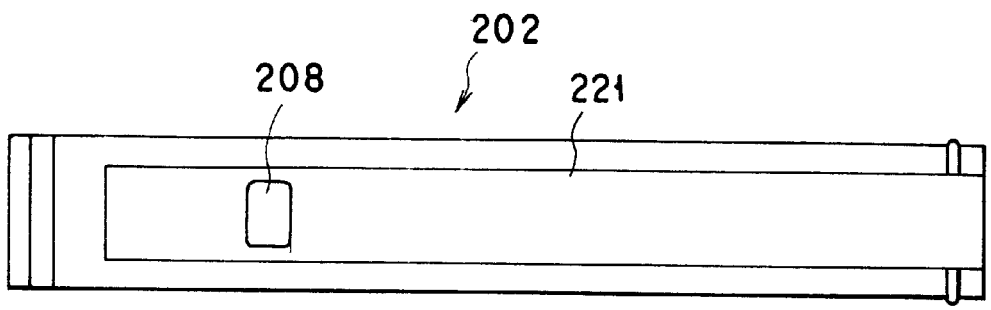
FIG. 29 is a plane view showing a housing of the sticking tool of FIG. 26.

A sticking tool 201 whose cross-section is shown in FIG. 26 is mainly used for sampling a fine amount of body fluids, such as blood, from the surface of a living body. The sticking tool 201 is constituted by a housing 202, a plunger 203 which slides inside the housing 202, a lancet 204 which is attached to the tip end of the plunger 203 and has a sticking needle 241 that extends toward the tip end, a stopper 205 connected to the rear end of the plunger 203, an adjusting mechanism 210 that contacts the stopper 205, and a sticking-use spring 206 used for shifting the plunger 203, the lancet 204 and the stopper 205 toward the tip. An engaging section 8 is installed on the inner face of the housing 202, and a stopping section 207, which engages the engaging section 208 so as to stop the plunger 203, the lancet 204 and the stopper 205 at a first position, is installed in the plunger 203.

Here, the first position refers to a state prior to the sticking operation onto the surface of a living body, and is shown in FIG. 26 more specifically.

The shape of the housing 202 is not particularly limited as long as it has a cylindrical shape as shown in FIG. 26; however, from the viewpoint of ease of gripping, it is preferable to provide it as a cylinder. Moreover, it is more preferable to provide a flat section 221 shown in a plan view of FIG. 29 on the periphery of the engaging section 208, because the engagement between the stopping section 207 and the engaging section 208 can be easily released without the need for observing it, merely by sliding the finger along the flat section 221.

The sticking-use spring 206, one end of which is connected to the plunger 203 and the other end of which is connected to a sticking-use spring fixing base 209 installed inside the housing, is inserted in a compressed state. However, the present invention is not intended to be limited to this structure, and one end may be connected to the lancet 204 or the stopper 205, while the other end may be directly connected to the inner face of the housing 202. Moreover, with respect to the sticking-use spring 206, any spring may be used as long as it allows the plunger 203, lancet 204 and stopper 205 to shift to the first position to the second position, and the shape thereof is not particularly limited; for example, in addition to a coil-shape spring as shown in the drawing, a plate-shape spring, etc. may be adopted, and the material thereof is not particularly limited. Here, at the first position, the sticking-use spring 206 is in a compressed state.

Here, the second position refers to a position at which the sticking needle 241 sticks the surface of a living body, and in this case, the state is not limited to a state in which the sticking needle protrudes from the tip end of the sticking tool 201 and, for example, it includes a state in which the tip end of the sticking tool 201 is pressed onto the surface of a living body so as to be ready for sticking, with the surface of the living body swells inside the tip end.

The stopping section 207 is installed in the plunger 203; however, the present invention is not intended to be limited to this structure, and it may be installed in the lancet 204 or the stopper 205. With respect to the shape thereof, instead of securing one end to the plunger 203, etc., a shape, such as a U-letter shape or a V-letter shape, for allowing both of the ends to be secured to the plunger 203, etc. may be adopted. In other words, any shape may be adopted as long as the plunger 203, the lancet 204 and the stopper 205 are stopped at the first position by the engagement with the engaging section 208 and the engagement with the engaging section 8 can be released by a movement. Moreover, in the case of the engaging section 208 that penetrates the housing 202 from the inner face to the outer face, which will be described later, it is preferable to design the stopping section 207 so that one portion thereof protrudes from the outer face of the housing 202 through the engaging section 208, from the viewpoint of the operation for releasing the engagement.

The engaging section 208 is not particularly limited as long as it engages the stopping section 207 installed on the inner face of the housing 202; however, it is preferable to provide it as a hole penetrating the housing 202 from the inner face to the outer face as is shown in the present embodiment. With this structure, it is possible to ensure the engagement with the stopping section 207, and also to easily release the engagement by pushing the stopping section 207.

The stopper 205 is connected to the rear end of the plunger 203 and provided with a stopper-side shift restriction mechanism 251. The stopper-side shift restriction mechanism 251 engages an adjustment-mechanism-side shift restriction mechanism 210a so that the plunger 203, the lancet 204 and the stopper 205, which have shifted from the first position, are stopped at the second position. Here, in the present embodiment, the stopper-side shift restriction mechanism 251 and the adjustment-mechanism-side shift restriction mechanism 101 are both provided as protrusions; however, the structures are not particularly limited, and another structure may be adopted in which one is provided as a protrusion and the other is provided as a recess, or in which the inner diameter or the outer diameter is gradually changed in the axial direction in both of the mechanisms so that they make a taper-shape engagement. Moreover, the stopper 205 is not necessarily provided as a member separated from the plunger 203 as described in the present embodiment, and it may be provided as an integral part of the plunger 203.

Since the lancet 204 is placed apart from the stopper 205, a shock, which is transmitted to the lancet when the plunger 203, the lancet 204 and the stopper 205 have been stopped at the second position from the first position, can be damped by the stopper 205. In other words, different from a conventional mechanism, since the lancet is not directly restricted in its movement, the shock is not directly transmitted to the lancet; therefore, it is possible to prevent an accidental separation of the sticking tool 1 from the hand of the operator by the shock, trembling of the sticking operation and unnecessary pain being given to the person whose body fluids are sampled.

With respect to the adjustment mechanism 210, any mechanism can be adopted as long as it is movable in the axial direction inside the housing 202 as shown in FIG. 26, with the stopper 205 being allowed to move inside thereof, and more specifically, one having a cylinder shape may be adopted. The above-mentioned adjustment-mechanism-side shift restriction mechanism 210a is installed in the adjustment mechanism 210. Moreover, it is preferable to design the adjustment mechanism 210 so as to have an uninserted portion 210b with respect to the housing 202, and with this arrangement, a driving force for axially rotating the adjustment mechanism 210 can be transmitted.

The uninserted portion 210b is preferably covered with a protection cover 211 so as to prevent the adjustment mechanism 210 from being shifted from the set position due to an erroneous operation. In this case, the protection cover 11 is preferably designed so as to have a structure and a material property in which the uninserted portion 210b is not rotated unless the operator intends to do so. For example, it may be removable upon operation of the uninserted portion 210b or it may have flexibility so as to allow the operator to pinch the uninserted portion 210b and to axially rotate it.

Figure 30:
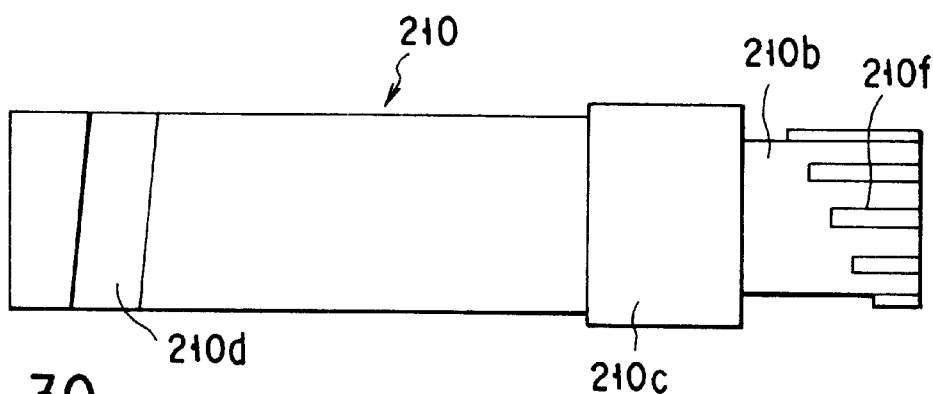
FIG. 30 is a front view of an adjusting mechanism of the sticking tool of FIG. 26.
Figure 31:
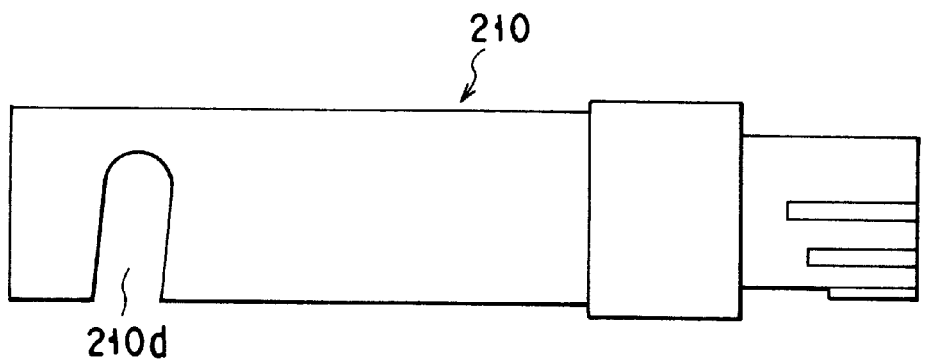
FIG. 31 is a plane view showing the adjusting mechanism of the sticking tool of FIG. 30.
Figure 32:
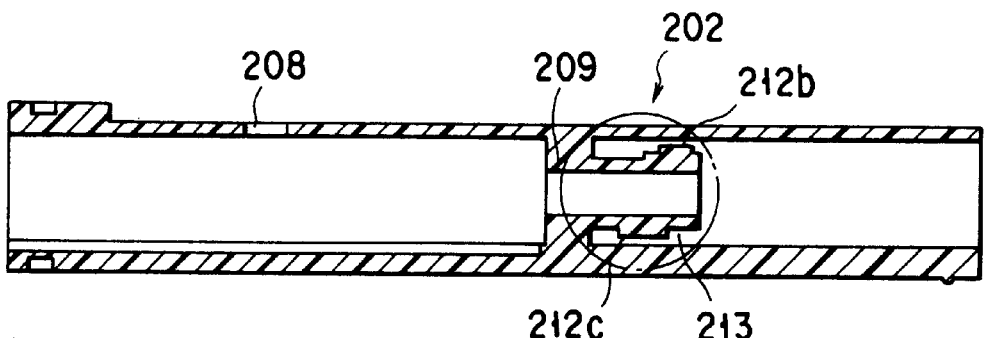
FIG. 32 is a cross-sectional view showing a housing of the sticking tool of FIG. 26.

In the present embodiment, the adjustment mechanism 210 has a structure whose front view is shown in FIG. 30 and whose plan view is shown in FIG. 31. Specifically, a helical groove 210d is formed on the peripheral portion thereof. This groove 210d allows a protruding member 212b installed in a connecting section which will be described later to relatively move along the inside thereof.

Figure 33:
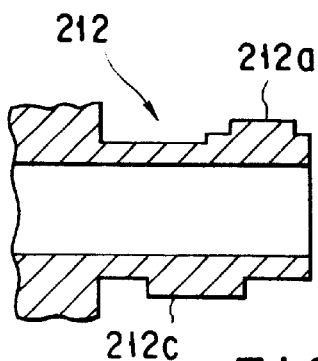
FIG. 33 is a connecting section (the portion in the circle in FIG. 32) provided in the housing of the sticking tool of FIG. 26.
Figure 34:
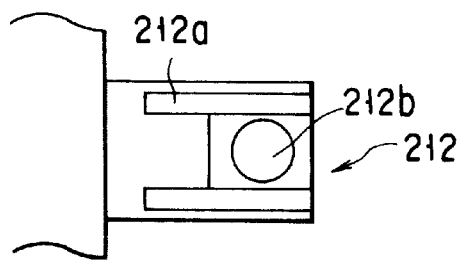
FIG. 34 is a plane view showing the connecting section of the sticking tool of FIG. 26.

Moreover, in the present embodiment, as illustrated in FIG. 34 showing its cross-section together with the housing 202 and FIG. 33 showing its enlarged cross section, the adjustment mechanism 210 extends in the rear-end direction from the sticking-use spring fixing base 209 installed on the inner face of the housing 202, and is fitted to the connecting section 212 which has a cylinder shape so as to allow the stopper 205 to slide therein.

Figure 35:
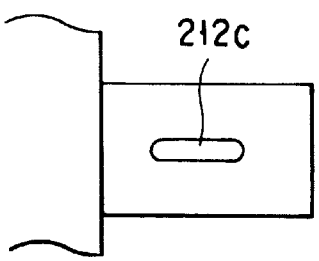
FIG. 35 is a bottom view showing the connecting section of FIG. 34.
Figure 36:
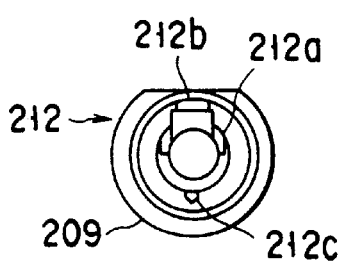
FIG. 36 is a left-side sectional view showing the connecting section of FIG. 34.

The connecting section 212 is provided with the protruding member 212b whose plan view is shown in FIG. 34 and whose left side view is shown in FIG. 36, and a fixing protrusion 212c whose bottom view is shown in FIG. 35. When the adjustment mechanism 210 is axially rotated, the protruding member 212b relatively moves inside the groove 210d, thereby allowing the adjustment mechanism 210 to move in the axial length direction. Thus, the second position of the plunger 203, etc. can be adjusted. The fixing protrusion 212c can fix the state of the adjustment mechanism 210 at the predetermined second position of the plunger, etc. by engaging the recess 210e formed in the inner face of the adjustment mechanism 210. Here, the fixing protrusion 212c is not necessarily placed diagonally to the protruding member 212b, and not limited to one position, it may be placed at a plurality of positions.

Figure 37:
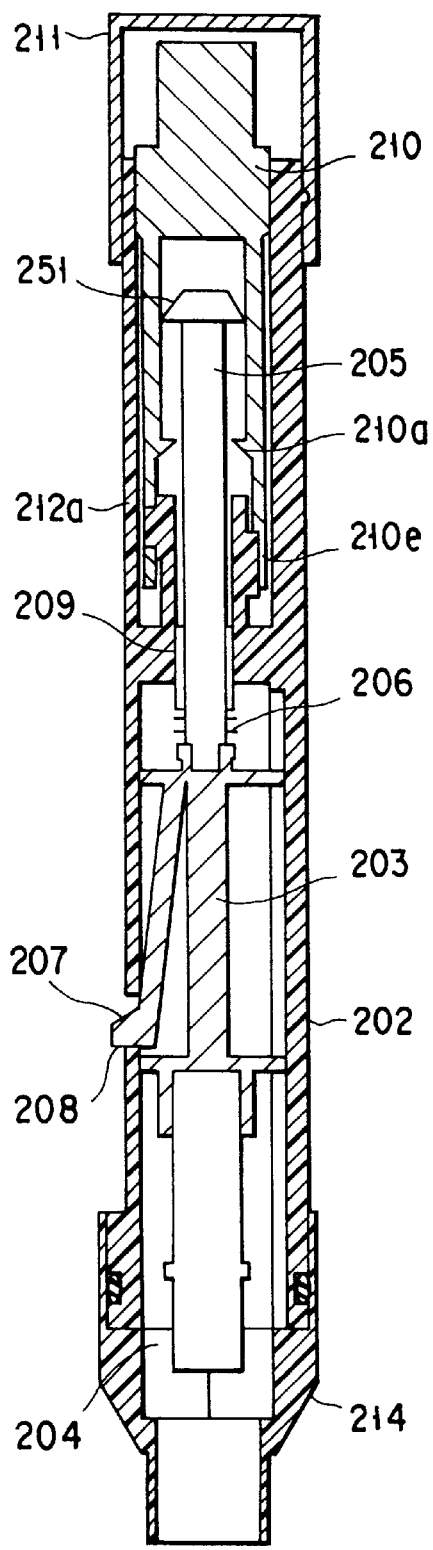
FIG. 37 is a cross-sectional view showing a state wherein the transfer or travel range of a plunger of the sticking tool of FIG. 26 from a first position to a second position is small.
Figure 38:
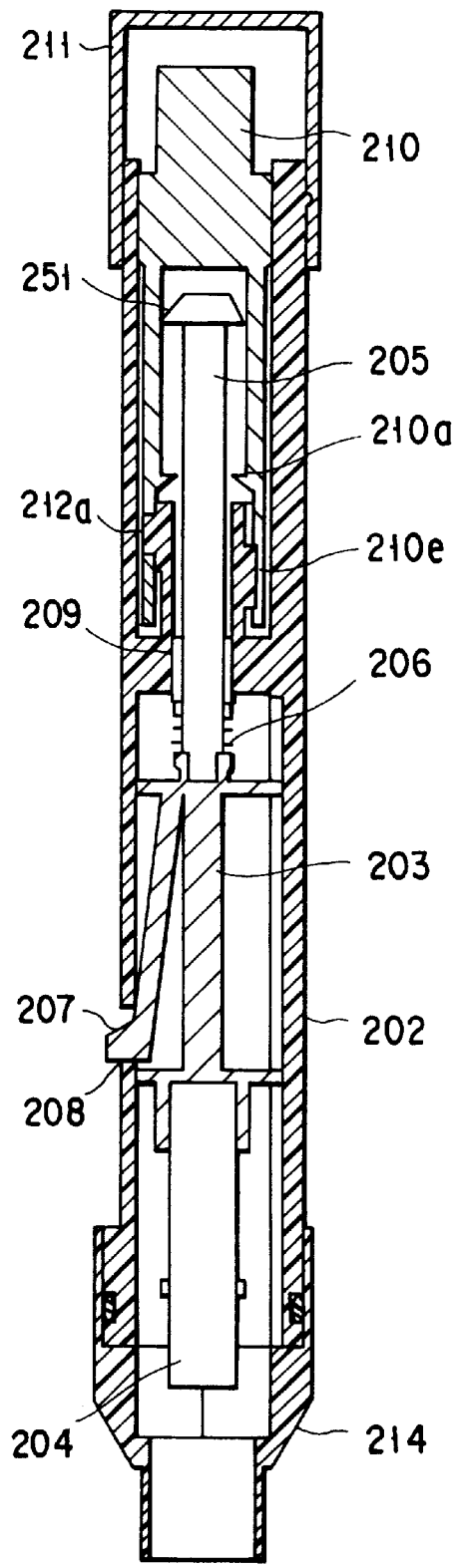
FIG. 38 is a cross-sectional view showing a state wherein the transfer or travel range of the plunger of the sticking tool of FIG. 26 from the first position to the second position is large.

The following description will discuss the relationship between the adjustment mechanism 210 and the stopper 205 more specifically. The shift range of the stopper 205, etc. from the first position to the second position is indicated by the position of the adjustment mechanism 210 in the length direction and distance X (see FIG. 26) from plane A (see FIG. 26) of the stopper-side shift restriction mechanism 51 and plane B (see FIG. 26) of the adjustment-mechanism-side shift restriction mechanism 210a. FIG. 37 shows a state in which the shift range from the first position to the second position is small, and FIG. 38 shows a state in which the shift range from the first position to the second position is large. Here, the position of the adjustment mechanism 210 in the length direction is determined by the position of the protruding member 212b of the connecting section 212 inside the helical groove 210d of the adjustment mechanism 210, which is given by axially rotating the adjustment mechanism 210. In other words, distance X is adjusted and determined by axially rotating the adjustment mechanism 210.

Moreover, the following description will discuss the relationship between the recess 210e formed in the inner face of the adjustment mechanism 210 and the fixing protrusion 212c that is placed in the connecting section 212 more specifically. For example, it is supposed that the difference in positions of the helical groove 210d in the axial length direction of the adjustment mechanism 210 (the difference between the state having a large range from the first position to the second position and the state having a small range from the first position to the second position) is set at 1 mm, and that five recesses 210e are formed in the inner face of the adjustment mechanism 210 with equal intervals (with 45-degree intervals around the central axis in the length direction of the sticking tool 201). In this case, distance X can be adjusted by 0.25 mm for each step. Moreover, if it is supposed that the difference in positions of the helical groove 210d in the axial length direction of the adjustment mechanism 210 (the difference between the state having a large range from the first position to the second position and the state having a small range from the first position to the second position) is set at 1 mm, and that recesses 210e are formed in the inner face of the adjustment mechanism 210 at positions with respective angles of 0 degree, 18 degrees, 54 degrees, 108 degrees, and 180 degrees, distance X can be adjusted not at equal intervals, but at predetermined values such as 0.1 mm, 0.2 mm, 0.3 mm and 0.4 mm.

Here, it is preferable to provide a mark 210f on the uninserted portion 210b so as to allow visual confirmation of a set value that is to be adjusted by the adjustment mechanism 210.

The connecting section 212 is preferably provided with one or two or more slits 212a that extend in the length direction. The installation of the slits 212a makes it possible to accept a distortion that occurs inside the adjustment mechanism 210 when the stopper-side shift restriction mechanism 251 and the adjustment-mechanism-side shift restriction mechanism 210a come into contact with each other. With this arrangement, it is possible to reduce vibration that occurs in the entire structure of the sticking tool 201 when the stopper-side shift restriction mechanism 251 and the adjustment-mechanism-side shift restriction mechanism 210a come into contact with each other. Therefore, it becomes possible to prevent an accidental separation of the sticking tool 201 from the hand of the operator by the vibration, trembling during the sticking operation and unnecessary pain being given to the person whose body fluids are sampled.

Moreover, the adjustment mechanism 210 is connected through the connecting section 212 so that the connection of the adjustment mechanism 210 is made with a space 213 between the outer face of the adjustment mechanism 210 from at least the vicinity of the adjustment-mechanism-side shift restriction mechanism 210a to the tip end and the inner face of the housing.

The space 213 makes it possible to accept a distortion that occurs outside the adjustment mechanism 210 when the stopper-side shift restriction mechanism 251 and the adjustment-mechanism-side shift restriction mechanism 210a come into contact with each other. With this arrangement, in the same manner as the installation of the slits 212a in the connecting section 212 as described above, it is possible to reduce vibration that occurs in the entire structure of the sticking tool 201 when the stopper-side shift restriction mechanism 251 and the adjustment-mechanism-side shift restriction mechanism 210a come into contact with each other. Therefore, it becomes possible to prevent an accidental separation of the sticking tool 201 from the hand of the operator by the vibration, trembling during the sticking operation and unnecessary pain being given to the person whose body fluids are sampled. Additionally, an outer diameter section 210c which is virtually identical to the inner diameter of the housing 202 is preferably attached to the adjustment mechanism 210; thus, it becomes possible to axially rotate the adjustment mechanism 210 stably even with the space 213.

In the present invention, the connecting section 212 is not necessarily provided, and another structure may be provided in which a protruding member corresponding to the protruding member 212b is attached to either one of the inner face of the housing 202 and the outer face of the adjustment mechanism 210 and a helical groove corresponding to the helical groove 210d is formed in the other so that the position of the adjustment mechanism 210 is adjusted by axially rotating the adjustment mechanism.

It is preferable to install a cap 214 on the tip end of the housing 202. This forms a structure in which the sticking needle 211 is not allowed to protrude outside the cap when the plunger 203, etc. is located at the first position, thereby making it possible to prevent the sticking needle 211 from erroneously hurting the hand or the finger. The installation method of the cap 214 and the housing 202 is not particularly limited, and a snap-in method and a screwing method by using threads are listed so as to allow easy removal. Here, an opening 214a is formed in the contact face to the surface of a living body of the cap 214, and its diameter is set in the range of not less than 1 mm to not more than 10 mm, and more preferably in the range of not less than 1 mm to not more than 6 mm, so as to carry out the sticking operation without limiting the portion to be stuck.

Figure 39:
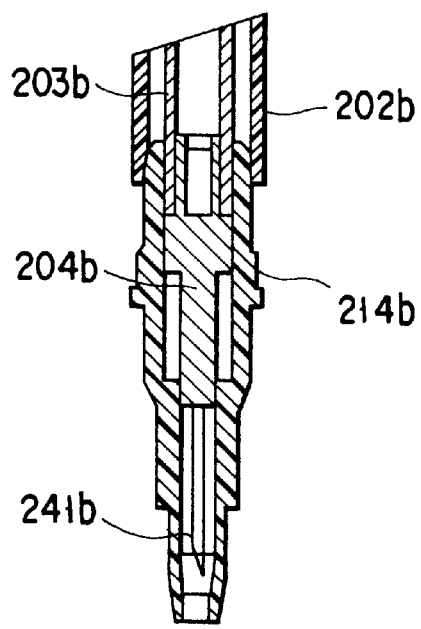
FIG. 39 is a cross-sectional view showing the tip end portion of the sticking tool of FIG. 26 wherein another form of cap is attached.

Moreover, the cap may have another structure as indicated by a cap 214b whose cross-sectional view of the tip portion is shown in FIG. 39. The cap 214b houses a lancet 204b which can slide inside thereof and to which a sticking needle 241b is connected. The cap 214b makes it possible to connect the other end of the lancet 204 to the plunger 203 when the cap 214b is connected to the housing 202b; thus, the same application as described in an explanation of the application of the present embodiment that will be given later is available.

In the present embodiment, it is preferable to respectively provide an axial direction groove 222 in the inner face of the housing 202 and a tremble-preventing protrusion 231 on the plunger 203. The tremble-preventing protrusion 231 shifts along the axial direction groove 222 so that the plunger 203 is allowed to move only in the axial direction in a stable manner without trembling in the axial rotation direction; therefore, this allows the sticking needle 241 to stick at an accurate position.

The materials of the above-mentioned constituent parts are not particularly limited, and they are appropriately selected from hard plastics, metals, etc. However, with respect to at least the sliding face of the plunger 203 against the inner face of the housing 202 or at least the sliding face of the housing 202 against the plunger 203, it is preferable to use a material, such as a thermoplastic elastomer and rubber, which can maintain the sliding face in an air-sealed state. By providing the air-sealed state, after having pressed the tip end of the housing 202 onto the surface of a living body and stuck the surface of the living body with the sticking needle 241, when the plunger 203 is returned from the second position to the first position, a space inside the housing 202, formed by the plunger 203 and the tip end sealed by the surface of a living body, is brought to a reduced-pressure state so that the surface of the living body is sucked and body fluids to be sampled are effectively sucked. Moreover, a suction means may be preliminarily provided so that the space inside the housing 202, formed by the plunger 203 and the tip end sealed by the surface of a living body, is brought to a reduced-pressure state, thereby making the surface of the living body swell into the housing 202. Then, the swelled surface may be stuck with the sticking needle 241 so as to effectively suck body fluids to be sampled.

In the case when the suction process is carried out after the sticking operation on the surface of a living body, upon movement of the plunger 203 to the second position, the space inside the housing 202, formed by the plunger 203 and the tip end sealed by the surface of a living body, tends to have a positive pressure, making the sticking process inoperable. For this reason, it is preferable to install a one-directional valve, such as a duck bill valve, in either the housing 202, the plunger 203, or the cap 214, so as to release the air inside the housing 202 causing the positive pressure out of the housing 202, or so as not to allow the outer air to flow into the housing 202 having a reduced pressure.

Next, an explanation will be given of the application of the present embodiment. First, the operator removes the protection cover 211, and sets the second position of the plunger 203, the lancet 204 and the stopper 205 which allows to suck a minimum amount of body fluids such as blood required for an inspection, that is, the shift distance of the sticking needle 241. Thus, it becomes possible to reduce a pain accompanying the sticking operation to a minimum level required. Once the adjustment mechanism 210 has been set, it is not necessary to frequently reset the setting; therefore, the use of the protection cover 11 makes it possible to prevent the sticking needle from being stuck deeper due to an erroneous change in the depth of sticking, erroneous blood sampling, and other misoperations.

Next, the lancet 204 having the sticking needle 241 is attached to the tip end of the plunger 203, and the plunger 203 with the lancet 204 attached thereto is pushed toward the rear end against the elastic force of the sticking-use spring 206 so that the stopping section 207 is engaged by the edge of the engaging section 208. At this time, the sticking-use spring 206 is maintained in a compressed state. Thus, preparation for the sticking operation onto the surface of a living body is completed (see FIG. 26).

Then, the opening 214a of the tip end of the cap 214 is pressed onto the surface of a living body such as the finger tip, and the stopping section 207 protruding from the engaging section 208 is pressed. This releases the engagement between the stopping section 207 and the engaging section 208, and the sticking-use spring 206, which has been compressed, extends with its elastic force so that the plunger 203 is shifted toward the tip end, the sticking needle 241 protrudes from the opening 214a of the cap 214, and carries out a sticking operation onto the surface 215 of a living body (see FIG. 27). At this time, the stopper 205 slides inside the housing 202 together with the plunger 203, the stopper-side shift restriction mechanism 251 of the stopper 205 comes into contact with the adjustment-mechanism-side shift restriction mechanism 210a of the adjustment mechanism 210 so that the shift of the plunger 203 toward the tip end is restricted; thus, the depth of sticking by the sticking needle 241 of the lancet 204 onto the surface of a living body is adjusted to a predetermined depth. After the sticking operation of the sticking needle 241 onto the surface of the living body, the sticking-use spring 208 returns to its natural length through damping movements, and the sticking needle is drawn from the surface of the living body and stored in the housing 202 (see FIG. 28).

As described above, the sticking tool 201 is designed so that the lancet 204 does not protrude from the opening 214a of the tip end of the cap 214 except that it is used for the sticking operation; therefore, it is possible to prevent the sticking needle from erroneously hurt the skin, etc., to prevent contagion, etc., and also to provide a highly safe device. With the stopper 205 and the adjustment mechanism, the sticking operation can be performed onto the predetermined sticking position with high reproducibility.

The sticking tool of the present invention is provided with the mechanism for adjusting the depth of sticking by the lancet; this allows the operator to set the depth of sticking suitable for obtaining a minimum amount of blood required for an inspection, and makes it possible to reduce a pain accompanying the sticking operation to a minimum level required.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-fluid inspection device which sticks a skin so as to obtain a fine amount of body fluids and measures ingredients of the body fluids, comprising:

a casing having an opening;

sticking means having a sticking needle that is allowed to protrude from the opening of the casing;

suction means which places at least a portion of a space inside the casing in a reduced-pressure state for sucking body fluids from a wound produced by the sticking means;

reduced-pressure releasing means for releasing the space inside the casing from the reduced-pressure state, the reduced-pressure releasing means being provided with a vent hole which allows the inside and the outside of the casing to communicate with each other and an opening and closing means for opening and closing the vent hole;

a chip which is detachably attached to the opening of the casing, and provided with test paper for absorbing the body fluids that have been sucked by the suction means;

measuring means for measuring ingredients of the body fluids that have been absorbed by the test paper; and display means for displaying results of measurements made by the measuring means, the display means being placed on one portion of a surface of the casing, wherein the sticking means, the suction means and the measuring means are installed inside the casing.

2. The body-fluid inspection device according to claim 1, further comprising evacuation means which, when the casing becomes a pressurized state at the time of sticking, releases an amount of air corresponding to the excessive pressure.

3. The body-fluid inspection device according to claim 2, wherein the opening and closing means comprises a wedge member, the evacuation means is constituted by a non-return valve that is installed in the vent hole so as to stop a force directed into the casing, and the wedge member allows the non-return valve to be opened and closed in the reverse direction.

4. The body-fluid inspection device according to claim 1, further comprising connecting means provided with a seal member for connecting the casing and the chip in an air-sealed state, the connecting means being installed in the opening of the casing.

5. The body-fluid inspection device according to claim 1, further comprising body-fluid guide means for guiding the body fluids that have been sucked to the test paper by capillary phenomenon, the body-fluid guide means being installed in the chip.

6. The body-fluid inspection device according to claim 1, further comprising release means for removing the chip, the release means being installed at the opening of the casing.

7. The body-fluid inspection device according to claim 1, wherein the sticking means comprises adjusting means for adjusting the depth of sticking by the sticking needle.

8. The body-fluid inspection device according to claim 1, which comprises:

a housing having an opening at the tip end thereof;

sticking means including a sticking plunger that is allowed to shift toward the tip end inside the housing with the sticking needle being attached thereto, and a first pressing means for pressing the sticking plunger toward the tip end;

suction means including a suction plunger that is provided with a seal member having an air-sealed property and that brings the housing to a reduced-pressure state upon shifting toward the base end, and a second pressing means for pressing the suction plunger toward the base end;

air-releasing means for releasing the housing which is in a reduced-pressure state to the atmospheric pressure; and operation means for carrying out at least a sticking process by the sticking needle and a pressure-reducing process inside the housing by an operation of the suction plunger, successively in this order or at the same time.

9. The body-fluid inspection device according to claim 1, which comprises:

a housing having an opening at the tip end thereof;

sticking means including a sticking plunger that is allowed to shift toward the tip end inside the housing with the sticking needle being attached thereto, and a first pressing means for pressing the sticking plunger toward the tip end;

suction means including a suction plunger that is provided with a seal member having an air-sealed property and that brings the housing to a reduced-pressure state upon shifting toward the base end, and a second pressing means for pressing the suction plunger toward the base end;

air-releasing means for releasing the housing which is in a reduced-pressure state to the atmospheric pressure; and operation means which carries out a sticking process by the sticking needle and a pressure-reducing process inside the housing by an operation of the suction plunger, successively in this order or at the same time, and then allows the housing to be released to the atmospheric pressure.

10. The body-fluid inspection device according to claim 1, which comprises:

a housing having a tip end that is opened;

a plunger to which a lancet having a sticking needle extending toward the tip end is attached, the plunger being allowed to slide inside the housing;

a stopper connected in the rear end direction of the plunger;

an adjustment mechanism which contacts the stopper; and a sticking-use spring for shifting the lancet, the plunger and the stopper toward the tip end of the housing, the sticking-use spring being connected to the plunger or the stopper, wherein: an engaging section is provided in the inner face of the housing;

a stopping section is formed in at least one of the lancet, the plunger and the stopper, the stopping section being allowed to engage the engaging section so as to stop the lancet, the plunger and the stopper at a first position; and after the lancet, the plunger and the stopper have shifted toward the tip end from the first position by the spring that is released from the engagement between the engaging section and the stopping section, the stopper comes into contact with the adjustment mechanism so that the shift of the lancet, the plunger and the stopper is stopped at a second position.

11. A sticking tool comprising:

a housing having an opening at the tip end thereof;

a sticking plunger that is allowed to shift toward the tip end inside the housing with the sticking needle being attached thereto;

first pressing means for pressing the sticking plunger toward the tip end;

a suction plunger that is provided with a seal member having an air-sealing property and that brings the housing to a reduced-pressure state upon shifting toward the base end;

second pressing means for pressing the suction plunger toward the base end;

air-releasing means for releasing the housing which is in a reduced-pressure state to the atmospheric pressure; and operation means for carrying out at least a sticking process by the sticking needle and a pressure-reducing process inside the housing by an operation of the suction plunger, successively in this order or at the same time.

12. A sticking tool comprising:

a housing having an opening at the tip end thereof;

a sticking plunger that is allowed to shift toward the tip end inside the housing with the sticking needle being attached thereto;

first pressing means for pressing the sticking plunger toward the tip end;

a suction plunger that is provided with a seal member having an air-sealing property and that brings the housing to a reduced-pressure state upon shifting toward the base end;

second pressing means for pressing the suction plunger toward the base end;

air-releasing means for releasing the housing which is in a reduced-pressure state to the atmospheric pressure; and operation means which carries out a sticking process by the sticking needle and a pressure-reducing process inside the housing by an operation of the suction plunger, successively in this order or at the same time, and then allows the housing to be released to the atmospheric pressure.

13. The sticking tool according to claim 11, wherein the sticking plunger has a first stopping section for making an engagement with the housing, and is allowed to shift toward the tip end by releasing the engagement of the first stopping section while being pressed by the first pressing means, so as to carry out a sticking operation.

14. The sticking tool according to claim 13, wherein the suction plunger has a second stopping section for making an engagement with the housing, and is allowed to shift toward the base end by releasing the engagement of the second stopping section while being pressed by the second pressing means, so as to carry out a suction operation inside the housing.

15. The sticking tool according to claim 14, wherein the operation means is provided with an operation button which carries out the releasing of the first stopping section and the releasing of the second stopping section in this order or at the same time.

16. The sticking tool according to claim 11, wherein the air-releasing means is automatically allowed to operate when the suction plunger has arrived at or approaches a limit position of shift on the base-end side.

17. The sticking tool according to claim 14, wherein the operation means has an operation button which carries out the releasing of the first stopping section and the releasing of the second stopping section in this order or at the same time, and then allows the air-releasing means to operate.

18. The sticking tool according to claim 15, further comprising a first protrusion and a second protrusion that respectively engage the first stopping section and the second stopping section, and a pressing member that is elastically deformed in accordance with the operation of the operation button.

19. The sticking tool according to claim 11, wherein the suction plunger is provided with a gasket which slides while being in contact with the inner face of the housing in an air-sealed state.

20. The sticking tool according to claim 11, wherein the air-releasing means is constituted by an air-releasing valve.

21. The sticking tool according to claim 20, wherein the air-releasing valve is provided with a vent opening, a seal member made of an elastic member capable of sealing the vent opening and an opening and closing mechanism for opening and closing the vent opening by deforming or shifting the seal member.

22. The sticking tool according to claim 20, wherein the air-releasing valve has a function as a relief valve for releasing air corresponding to an excessive pressure when the housing is in a pressurized state.

23. The sticking tool according to claim 11, further comprising an adjustment mechanism for adjusting the depth of sticking made by the sticking needle.

24. The sticking tool according to claim 11, wherein an operation direction in which the sticking plunger is shifted so as to carry out a sticking operation and a shifting direction of the sticking plunger are different from each other.

25. The body-fluid inspection device according to claim 1, further comprising evacuation means which, when the casing becomes a pressurized state at the time of sticking, releases an amount of air corresponding to the excessive pressure.

26. The sticking tool according to claim 12, wherein the sticking plunger has a first stopping section for making an engagement with the housing, and is allowed to shift toward the tip end by releasing the engagement of the first stopping section while being pressed by the first pressing means, so as to carry out a sticking operation.

27. The sticking tool according to claim 12, wherein the air-releasing means is automatically allowed to operate when the suction plunger has arrived at or approaches a limit position of shift on the base-end side.

28. The sticking tool according to claim 17, further comprising a first protrusion and a second protrusion that respectively engage the first stopping section and the second stopping section, and a pressing member that is elastically deformed in accordance with the operation of the operation button.

29. The sticking tool according to claim 12, wherein the suction plunger is provided with a gasket which slides while being in contact with the inner face of the housing in an air-sealed state.

30. The sticking tool according to claim 12, wherein the air-releasing means is constituted by an air-releasing valve.

31. The sticking tool according to claim 21, wherein the air-releasing valve has a function as a relief valve for releasing air corresponding to an excessive pressure when the housing is in a pressurized state.

32. The sticking tool according to claim 12, further comprising an adjustment mechanism for adjusting the depth of sticking made by the sticking needle .

33. The sticking tool according to claim 12, wherein an operation direction in which the sticking plunger is shifted so as to carry out a sticking operation and a shifting direction of the sticking plunger are different from each other.

* * * * *

UNITED STATES PATENT AND TRADEMARK OFFICE
CERTIFICATE OF CORRECTION

PATENT NO. : 6,261,245 B1
DATED : July 17, 2001
INVENTOR(S) : Eiji Kawai et al.

It is certified that error appears in the above-identified patent and that said Letters Patent is hereby corrected as shown below:

<u>Column 29,</u>
Line 22, "11" is changed to -- 211 --.
Line 55, "208" is changed to -- 206 --.

Signed and Sealed this

Fourteenth Day of May, 2002

*Attest:*

*Attesting Officer*

JAMES E. ROGAN
*Director of the United States Patent and Trademark Office*